United States Patent
Riley et al.

(10) Patent No.: US 12,017,967 B2
(45) Date of Patent: Jun. 25, 2024

(54) METHODS FOR CARBON CAPTURE AND INCREASING YIELD OF PLANTS

(71) Applicant: Loam Bio Pty Ltd, Orange (AU)

(72) Inventors: Ray Riley, St. Paul, MN (US); Andres Reyes, St. Paul, MN (US); Abed Chaudhury, Orange (AU); Suresh Subashchandrabose, Orange (AU); Ahsanul Haque, Orange (AU); Neeraj Purushotham, Orange (AU); Raghvendra Sharma, Orange (AU); Tegan Nock, Orange (AU); Gyongyver Korosi, Orange (AU); Brooke Bruning, Orange (AU); Grace Scott, Orange (AU); Venkatachalam Lakshmanan, St. Paul, MN (US)

(73) Assignee: Loam Bio Pty Ltd, Orange (AU)

( * ) Notice: Subject to any disclaimer, the term of this patent is extended or adjusted under 35 U.S.C. 154(b) by 0 days.

(21) Appl. No.: 18/406,089

(22) Filed: Jan. 6, 2024

(65) Prior Publication Data
US 2024/0150253 A1     May 9, 2024

Related U.S. Application Data

(63) Continuation of application No. 18/565,464, filed as application No. PCT/US2022/031487 on May 30, 2022.

(60) Provisional application No. 63/195,109, filed on May 31, 2021, provisional application No. 63/195,110, filed on May 31, 2021, provisional application No. 63/244,474, filed on Sep. 15, 2021.

(51) Int. Cl.
| | |
|---|---|
| C05F 11/08 | (2006.01) |
| A01H 3/00 | (2006.01) |
| A01N 63/30 | (2020.01) |
| C12N 1/14 | (2006.01) |
| C12R 1/645 | (2006.01) |
| C12R 1/885 | (2006.01) |

(52) U.S. Cl.
CPC ............. C05F 11/08 (2013.01); A01H 3/00 (2013.01); A01N 63/30 (2020.01); C12N 1/145 (2021.05); C12R 2001/645 (2021.05); C12R 2001/885 (2021.05)

(58) Field of Classification Search
None
See application file for complete search history.

(56) References Cited

FOREIGN PATENT DOCUMENTS

| | | |
|---|---|---|
| CN | 101643705 | 2/2010 |
| CN | 101643705 | 12/2011 |
| CN | 110129242 | 8/2019 |
| CN | 113337421 | 9/2021 |
| WO | 02065836 A2 | 8/2002 |
| WO | 2007/107000 | 9/2007 |
| WO | 2019/084324 A1 | 5/2019 |
| WO | 2019084324 | 5/2019 |
| WO | 22174313 | 8/2022 |
| WO | 2022/256275 | 12/2022 |

OTHER PUBLICATIONS

Dastogeer et al., "A simple and rapid in vitro test for large-scale screening of fungal endophytes from drought-adapted Australian wild plants for conferring water deprivation tolerance and growth promotion in Nicotiana benthamiana seedlings", Archives of Microbiology, 2017, vol. 199, p. 1357-1370.
Prestop Label EPA Reg 06137-00013-20160908.
J.C. Sutton et al., Evaluation of the Fungal Endophyte Clonostachys rosea as an Inoculant to Enhance Growth, Fitness and Productivity of Crop Plants. Proc. IVth IS on Seed, Transplant and Stand Establishment of Hort. Crops Ed.: D.I. Leskovar Acta Hort. 782, ISHS 2008.
Weil, Raymond R. & Brady, Nyle C. The Nature and Properties of Soils, 15th Edition, Pearson Edition, 2017, Chapters 1 to 4, 6, 11, 12 and 20.
Cotrufo, M.F., Renally, M.G., Haddix, M.L. et al. Soil carbon storage informed by particulate and mineral-associated organic matter. Nat. Geosci. 12, 989-994 (2019).
Charman, P. E. V & Murphy, B. W 2007, Soils: their properties and management / editors, P.E.V. Charman, B.W. Murphy. Oxford University Press Melbourne.
Rhizobial Inoculants Fact Sheet Grains Research & Development Corporation, University of Adelaide Aug. 2016.

(Continued)

*Primary Examiner* — Alton N Pryor
(74) *Attorney, Agent, or Firm* — Adam Lunceford

(57) ABSTRACT

A method of increasing organic carbon in a soil is disclosed. The method includes inoculating the soil and/or a plant growing in the soil with one or more fungal strains from at least one genus selected from the group consisting of *Acrocalymma, Clonostachys, Leptodontidium, Periconia, Phaeosphaeria, Thozetella, Trichoderma*, and a combination thereof, wherein the one or more fungal strains are in an amount effective to increase organic carbon in the soil compared to a non-inoculated control soil. Also disclosed is a method of enhancing plant growth, comprising: applying to a plant, a plant part, or the locus surrounding the plant with one or more fungal strains from at least one genus selected from the group consisting of *Acrocalymma, Clonostachys, Leptodontidium, Periconia, Phaeosphaeria, Thozetella, Trichoderma*, and a combination thereof in an amount effective to enhance the growth of the plant as compared to an untreated control plant.

27 Claims, 6 Drawing Sheets

Specification includes a Sequence Listing.

(56) References Cited

OTHER PUBLICATIONS

Jane M.-F. Johnson; Alan J. Franzluebbers; Sharon Lachnicht Weyers; Donald C. Reicosky (2007). Agricultural opportunities to mitigate greenhouse gas emissions. , 150(1), 0-124.

Gehlot, Praveen; Singh, Joginder (2018). Fungi and their Role in Sustainable Development: Current Perspectives || Carbon Sequestration and the Significance of Soil Fungi in the Process. 10.1007/978-981-13-0393-7(Chapter 26), 467-482.

Ellen L. Fry, Jonathan R. De Long, Richard D. Bardgett, Chapter 2—Plant Communities as Modulators of Soil Carbon Storage, Editor(s): Brajesh K. Singh, Soil Carbon Storage, Academic Press, 2018, pp. 29-71.

Kallenbach, C.M., et al., Microbial physiology and necromass regulate agricultural soil carbon accumulation, Soil Biology & Biochemistry (2015).

Sabine Ravnskov, Birgit Jensen, Inge M.B. Knudsen, Lars Bødker, Dan Funck Jensen, Leszek Karliński, John Larsen, Soil inoculation with the biocontrol agent Clonostachys rosea and the mycorrhizal fungus Glomus intraradices results in mutual inhibition, plant growth promotion and alteration of soil microbial communities, Soil Biology and Biochemistry, vol. 38, Issue 12, 2006, pp. 3453-3462.

LALSTOP—G48-WG Specimen-Label US EN Mar. 2020.

In the Matter of Australian Patent Application No. 2023202250 in the name of Loam Bio Pty Ltd-and-Opposition thereto by Jones Tulloch Pty Ltd; Statement of Grounds and Particulars, 20 pages 2023.

He et al. Plant Growth and Soil Microbial Impacts of Enhancing Licorice With Inoculating Dark Septate Endophytes Under Drought Stress. Frontiers in Microbiology. Oct. 9, 2019, vol. 10, No. 2277, p. 1-16.

Gen Bank Accession No. KF494164.1 "Acrocalymma vagum isolate TVD_Fungal-Culture166 internal transcribed spacer 1, partial sequence; 5.8S ribosomal RNA gene and internal transcribed spacer 2, complete sequence; and 28S ribosomal RNA gene, partial sequence" Jan. 31, 2017 [online]. [Retrieved on Oct. 10, 2022]. Retrieved from the internet: <URL:https://www.ncbi.nlm.nih.gov/nuccore/KF494164>; p. 1-2.

Gen Bank Accession No. KF494167.1 "Acrocalymma vagum isolate TVD_Fungal-Culture169 internal transcribed spacer 1, partial sequence; 5.8S ribosomal RNA gene and internal transcribed spacer 2, complete sequence; and 28S ribosomal RNA gene, partial sequence" Jan. 31, 2017 [online]. [Retrieved on Oct. 10, 2022]. Retrieved from the internet: <URL:https://www.ncbi.nlm.nih.gov/nuccore/KF494167>; p. 1-2.

International Search Report and Written Opinion of the International Searching Authority for International Patent Application No. PCT/US2022/031487, 17 pages.

METHODS FOR CARBON CAPTURE AND INCREASING YIELD OF PLANTS

CROSS REFERENCE TO RELATED APPLICATIONS

This application is a Continuation Application of U.S. patent application Ser. No. 18/565,464, filed Nov. 29, 2023, which is a U.S. National Stage of International Application No. PCT/US2022/031487, filed on May 30, 2022, which claims the benefit of U.S. Provisional Patent Application No. 63/195,109, filed on May 31, 2021; U.S. Provisional Patent Application No. 63/195,110, filed on May 31, 2021; and U.S. Provisional Patent Application No. 63/244,474, filed on Sep. 15, 2021; the contents of each of which are incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled LOAM-F002WO_Sequence_Listing.txt, 10,880 bytes in size, generated on May 27, 2022, and filed via EFS-Web, is provided in lieu of a paper copy. This Sequence Listing is incorporated by reference into the specification for its disclosures.

TECHNICAL FIELD

The present disclosure relates to methods and compositions for increasing carbon content in soil, mitigating atmospheric carbon dioxide, and increasing plant yield.

BACKGROUND

Carbon dioxide and methane absorb and retain heat in the atmosphere, and therefore both gases play a pivotal role in the greenhouse effect. As methane is much more short-lived than carbon dioxide, carbon dioxide is often considered to be more important than that of methane to the greenhouse effect.

The life cycle of carbon includes the removal of carbon dioxide from the atmosphere by plants through photosynthesis. During the process of photosynthesis, the carbon dioxide gets absorbed through stroma of leaves, and the carbon dioxide is further converted into sugars. Such sugars become nutrients for plants and microbes present in the soil. Carbon enters back into the atmosphere in the form of carbon dioxide by respiration and combustion. Hence, a balanced amount of release and absorption of the carbon dioxide is an essential step for balancing the ecosystem.

Human activities such as combustion of fuels, overpopulation, forest degradation, soil erosion, etc. have led to an increase in atmospheric carbon dioxide. Approaches for sequestering carbon dioxide from the atmosphere therefore present an important component of a strategy for reducing or controlling atmospheric carbon dioxide. However, for this to be successful, there must also be a reduction in the release of carbon dioxide from soil back into the atmosphere.

Decay of plants, animals, and microbes into the soil can lead to the build-up of soil organic carbon (SOC), an essential nutrient which promotes physical stability of the structure of the soil, soil aeration, water drainage and retention, thus reducing soil erosion and nutrient leaching. However, intensive cultivation has also led to a decline in SOC, eventually making the land unsuitable for commercial crop production. As such, the benefits associated with SOC can be seen as two-fold, namely, the sequestration of atmospheric carbon, provided the carbon is retained by the soil, and the overall improvement of the soil quality.

It would be advantageous to develop compositions, treatments and methods for increasing soil carbon in a manner that will produce more stable carbon in the soil by sequestering atmospheric carbon, as well as provide benefits to commercial crop plants.

SUMMARY

The inventors have found that some species of fungi, and in particular endophytic fungi, are capable of both fixing carbon and stabilising it as soil organic carbon, and increasing the yield of crop plants, when the plant is inoculated with the fungus.

In certain aspects, the disclosure provides a method of increasing organic carbon in a soil, comprising: inoculating the soil and/or a plant growing in the soil with one or more fungal strains from at least one genus selected from the group consisting of *Acrocalymma, Clonostachys, Leptodontidium, Periconia, Phaeosphaeria, Thozetella, Trichoderma*, and a combination thereof, wherein the one or more fungal strains are in an amount effective to increase organic carbon in the soil compared to a non-inoculated control soil.

In other aspects, the disclosure provides a method of increasing organic carbon in a soil, comprising: inoculating the soil and/or a plant growing in the soil with one or more fungal strains, wherein the one or more fungal strains are from at least one fungal species having a nuclear ribosomal internal transcribed spacer 2 (ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19; and the one or more fungal strains are in an amount effective to increase organic carbon in the soil compared to a non-inoculated control soil. In one aspect, the nuclear ribosomal internal transcribed spacer 2 (ITS2) sequence is at least 80%, at least 85%, at least 90%, at least 95%, at least 96%, at least 97%, at least 98%, or at least 99% identical to the nucleotide sequence of SEQ ID No: 1, 2, 3, 4, 5, 6, 7, 8, 9, 10, 11, 12, 13, 14, 15, 16, 17, 18, or 19.

In certain aspects, the one or more fungal strains are from a species selected from the group consisting of *Acrocalymma vagum, Clonostachys rosea, Leptodontidium orchidicola, Periconia* sp., *Periconia macrospinosa, Phaeosphaeria luctuosa, Phaeosphaeria vagans, Thozetella nivea, Trichoderma hamatum, Trichoderma longipile, Trichoderma spirale*, and a combination thereof.

In one aspect, the one or more fungal strains are selected from the group consisting of *Acrocalymma vagum* DMTR-CTR-11556 (NMI Accession No. V22/006357), *Clonostachys rosea* DMTR-CTR-US-173 (ATCC Accession No. PTA-127299), *Clonostachys rosea* DMTR-CTR-1081 (NMI Accession No. V22/003495), *Leptodontidium orchidicola* DMTR-CTR-4873 (NMI Accession No. V22/003497), *Periconia* sp. DMTR-CTR-6649 (NMI Accession No. V22/006356), *Periconia macrospinosa* DMTR-CTR-US-125 (ATCC Accession No. PTA-127300), *Periconia macrospinosa* DMTR-CTR-1852 (NMI Accession No. V22/006358), *Phaeosphaeria luctuosa/vagans* DMTR-CTR-3044 (NMI Accession No. V22/006355), *Thozetella nivea* DMTR-CTR-2359 (NMI Accession No. V22/003496), *Trichoderma hamatum* DMTR-CTR-US-73 (ATCC Accession No. PTA-127301), *Trichoderma longipile/spirale* DMTR-CTR-1291 (NMI Accession No. V22/006354), and a combination thereof.

In yet other aspects, the method further comprises an initial step of identifying the soil as having a soil organic carbon (SOC) level below a threshold. In one aspect, the threshold is a SOC level below 5%, 4%, 3%, 2%, 1%, 0.9%, 0.8%, 0.7%, 0.6%, 0.5%, 0.4%, 0.3%, 0.2%, or 0.1%.

In some aspects, the soil and/or plant are non-native to the one or more fungal strains. In one aspect, the non-native plant is selected from the group consisting of wheat, rice, corn (maize), rye, oats, barley, sorghum, millet, flax, hemp, jute, cotton, soybeans, alfalfa, clover, peanuts, lentils, lupins, peas, and chickpea.

In certain aspects, the disclosure provides a method of enhancing plant growth, comprising: applying to a plant, a plant part, or the locus surrounding the plant, one or more fungal strains from at least one genus selected from the group consisting of *Acrocalymma, Clonostachys, Leptodontidium, Periconia, Phaeosphaeria, Thozetella, Trichoderma*, and a combination thereof in an amount effective to enhance the growth of the plant as compared to an untreated control plant. The term "enhance" as used herein means to increase or improve a property, characteristic, or value.

In other aspects, the disclosure provides a method of enhancing plant growth, comprising: applying to a plant, a plant part, or the locus surrounding the plant, one or more fungal strains, wherein the one or more fungal strains are from at least one fungal species having a nuclear ribosomal internal transcribed spacer 2 (ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19; and the one or more fungal species are in an amount effective to enhance the growth of the plant as compared to an untreated control plant.

In some aspects, the plant exhibits at least one of increased root number, increased root length, increased root mass, increased root volume, increased leaf area, increased leaf number, increased pod number, increased plant height, increased shoot mass, increased chlorophyll content, increased nodulation, and increased yield, as compared to an untreated control plant.

In yet other aspects, the disclosure provides a method for sequestering atmospheric carbon for storage as organic carbon in a soil, comprising: inoculating the soil and/or a plant growing in the soil with one or more fungal strains from the group consisting of *Acrocalymma, Clonostachys, Leptodontidium, Periconia, Phaeosphaeria, Thozetella, Trichoderma*, and a combination thereof, wherein the one or more fungal strains are in an amount effective to increase sequestered atmospheric carbon in the soil compared to a non-inoculated control soil.

In another aspect, the disclosure provides a method for sequestering atmospheric carbon for storage as organic carbon in a soil, comprising: inoculating the soil and/or a plant growing in the soil with one or more fungal strains, wherein the one or more fungal strains are from at least one fungal species having a nuclear ribosomal internal transcribed spacer 2 (ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19; and the one or more fungal strains are in an amount effective to increase sequestered atmospheric carbon in the soil compared to a non-inoculated control soil.

In certain aspects, the disclosure provides a cell or a biologically pure culture of one or more fungal strains selected from the group consisting of *Acrocalymma vagum* DMTR-CTR-11556 (NMI Accession No. V22/006357), *Clonostachys rosea* DMTR-CTR-US-173 (ATCC Accession No. PTA-127299), *Clonostachys rosea* DMTR-CTR-1081 (NMI Accession No. V22/003495), *Leptodontidium orchidicola* DMTR-CTR-4873 (NMI Accession No. V22/003497), *Periconia* sp. DMTR-CTR-6649 (NMI Accession No. V22/006356), *Periconia macrospinosa* DMTR-CTR-US-125 (ATCC Accession No. PTA-127300), *Periconia macrospinosa* DMTR-CTR-1852 (NMI Accession No. V22/006358), *Phaeosphaeria luctuosa/vagans* DMTR-CTR-3044 (NMI Accession No. V22/006355), *Thozetella nivea* DMTR-CTR-2359 (NMI Accession No. V22/003496), *Trichoderma hamatum* DMTR-CTR-US-73 (ATCC Accession No. PTA-127301), and *Trichoderma longipile/spirale* DMTR-CTR-1291 (NMI Accession No. V22/006354).

In another aspect, the agricultural composition comprises the cell or a biologically pure culture and, optionally, an agriculturally acceptable carrier. In some aspects, the agricultural composition is applied or coated on at least a portion of an outer surface of a plant, plant part or plant seed.

In one aspect, the disclosure provides a method of increasing soil organic carbon in a soil and/or increasing yield of a crop plant, the method comprising inoculating the soil and/or the plant with an effective amount of one or more fungal species from at least one genus selected from *Acrocalymma, Clonostachys, Leptodontidium, Periconia, Phaeosphaeria, Thozetella*, and *Trichoderma*, and a combination thereof.

In another aspect, the disclosure provides a method of increasing soil organic carbon and/or increasing yield of a crop plant, the method comprising inoculating the soil and/or the plant with an effective amount of one or more fungal species, wherein the one or more fungal species has a nuclear ribosomal internal transcribed spacer 2(ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19.

In another aspect, the disclosure provides a composition for increasing soil organic carbon in a soil and/or increasing yield of a crop plant, the composition comprising one or more fungal species from at least one genus selected from *Acrocalymma, Clonostachys, Leptodontidium, Periconia, Phaeosphaeria, Thozetella*, and *Trichoderma*, and a combination thereof.

In certain aspects, the disclosure provides a composition for increasing soil organic carbon in a soil and/or increasing yield of a crop plant, the composition comprising one or more fungal species having a nuclear ribosomal internal transcribed spacer 2(ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19.

The inoculation of the one or more fungal species may be achieved by direct addition to a cultivated soil prior to sowing seeds or planting seedlings that are coated or partially coated with one or more fungal species such that the fungi will become associated with, or grow proximal to, or grow into the roots of a crop plant as the crop matures. Thus, a microbial treatment (e.g., fungal inoculation) associated with a crop plant is one in which microbes will become associated with, or grow proximal to, or grow into the roots of a crop plant as the crop matures.

In one aspect, the disclosure provides a microbial treatment to be deployed in soil and/or associated with a crop plant, the treatment comprising: one or more fungal species from at least one genus selected from *Acrocalymma, Clonostachys, Leptodontidium, Periconia, Phaeosphaeria, Thozetella, Trichoderma*, and a combination thereof, wherein the deployment of said treatment has one or more desirable effects selected from the group consisting of increasing the sequestration of atmospheric carbon for storage as stable carbon in the soil, providing agronomic benefits to said crop plants, increasing the levels of stable carbon in the soil, and increasing the soil aggregate stability of the soil.

In yet another aspect, the disclosure provides a microbial treatment to be deployed in soil and/or associated with a crop plant, the treatment comprising: one or more fungal species having a nuclear ribosomal internal transcribed spacer 2(ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19, wherein the deployment of said treatment has one or more desirable effects selected from the group consisting of increasing the sequestration of atmospheric carbon for storage as stable carbon in the soil, providing agronomic benefits to said crop plants, increasing the levels of stable carbon in the soil, and increasing the soil aggregate stability of the soil.

In other aspects, the disclosure provides a method for sequestering atmospheric carbon for storage as stable carbon in soil, the method comprising deploying a treatment comprising one or more fungal species from at least one genus selected from *Acrocalymma, Clonostachys, Leptodontidium, Periconia, Phaeosphaeria, Thozetella, Trichoderma*, and a combination thereof, in said soil and/or associating said fungus with a crop plant being cultivated in said soil.

In some aspects, the disclosure provides a method for sequestering atmospheric carbon for storage as stable carbon in soil, the method comprising deploying a treatment comprising one or more fungal species, wherein the one or more fungal species having a nuclear ribosomal internal transcribed spacer 2(ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19.

In other aspects, the disclosure provides a plant, plant part or plant seed associated with a composition comprising: one or more isolated fungal strains from at least one genus selected from the group consisting of *Acrocalymma, Clonostachys, Leptodontidium, Periconia, Phaeosphaeria, Thozetella, Trichoderma*, and a combination thereof; and an agriculturally acceptable carrier; wherein the composition is applied or coated on at least a portion of an outer surface of the plant, plant part or plant seed.

In yet other aspects, the disclosure provides a plant, plant part or plant seed associated with a composition comprising: one or more isolated fungal strains from at least one fungal species having a nuclear ribosomal internal transcribed spacer 2 (ITS2) sequence that is at least 90% identical to the nucleotide sequence of SEQ ID No: 1, 2, 3, 4, 5, 6, 7, 8, 9, 10, 11, 12, 13, 14, 15, 16, 17, 18, or 19; and an agriculturally acceptable carrier; wherein the composition is applied or coated on at least a portion of an outer surface of the plant, plant part or plant seed.

In some aspects, (a) the composition is formulated as a solid, liquid or gel; (b) the composition is formulated as a powder, pellet or granules; or (c) the composition is formulated as an emulsion, colloid, suspension or solution.

In other aspects, the agriculturally acceptable carrier confers at least one beneficial characteristic to the composition. In one aspect, the beneficial characteristic is selected from the group consisting of improved efficacy, stability, wetting, flowability, and coating onto the plant, plant part or plant seed relative to a control composition lacking the agriculturally acceptable carrier.

In yet other aspects, the one or more fungal strains are present in the composition at a concentration of at least $10^1$ CFU per millilitre or gram, at least $10^2$ CFU per millilitre or gram, at least $10^3$ CFU per millilitre or gram, at least $10^4$ CFU per millilitre or gram, at least $10^4$ CFU per millilitre or gram, or at least $10^5$ CFU per millilitre or gram. In one aspect, the one or more fungal strains are present in the composition at a concentration of at least $10^3$ CFU per millilitre or gram.

In some aspects, the one or more fungal strains are present in the composition at a concentration of $10^2$ to $10^{12}$ CFU/g, $10^3$ to $10^{12}$ CFU/g, $10^4$ to $10^{12}$ CFU/g, $10^5$ to $10^{12}$ CFU/g, $10^6$ to $10^{12}$ CFU/g, $10^7$ to $10^{12}$ CFU/g, $10^8$ to $10^{12}$ CFU/g, or $10^9$ to $10^{12}$ CFU/g.

In certain aspects, the disclosure provides a bag or container comprising plant seed disclosed herein. In other aspects, the disclosure provides a kit comprising plant seed disclosed herein.

DETAILED DESCRIPTION

Figure 1:
FIG. 1 depicts a photograph showing the phenotype observed with untreated control soybean plants and soybean plants inoculated with *Leptodontidium orchidicola* DMTR-CTR-4873.

The present disclosure relates to methods and related technologies for increasing soil organic carbon in a soil and/or increasing yield of a crop plant. The method comprises inoculating the soil and/or the plant with an effective amount of one or more compatible, non-pathogenic strains of fungal species from at least one genus selected from *Acrocalymma, Clonostachys, Leptodontidium, Periconia, Phaeosphaeria, Thozetella*, and *Trichoderma*, and a combination thereof.

It will be appreciated that the strains of fungi will be fungal strains that are crop-compatible with the crop plant to which they are to be applied, but the crop need not necessarily be a native host of the fungi. A fungal strain that is crop-compatible with a crop plant is a strain that is non-pathogenic to that crop plant. Methods for assessing whether a strain of fungus is non-pathogenic to a particular crop plant is known in the art.

An increase in soil organic carbon is an increase in the amount of organic carbon in soil associated with the crop plant inoculated with the one or more fungal species relative to the amount of organic carbon in uninoculated soil. In this context, the soil associated with the crop plant is soil surrounding the roots of the crop plant and from which the crop plant derives nutrients. An increase in plant yield is an increase in fruit, grain or vegetative tissue production of the plant relative to that of a plant that has not been treated with the one or more fungal species described herein. For example, an increase in yield of a soybean plant is an increase in the number and/or weight of seed pods produced by a soybean plant relative to that of an untreated soybean plant.

The inventors have found that growing a crop plant that has been inoculated with crop-compatible fungal strains of species selected from the genus selected from *Acrocalymma, Clonostachys, Leptodontidium, Periconia, Phaeosphaeria, Thozetella*, and *Trichoderma*, and a combination thereof, results in an increase in soil organic carbon and/or an increase in yield of crop plants.

The inventors have found that various crop plants inoculated with fungal species, and in particular, endophytic fungal species, exhibit increased yield relative to uninoculated plants. The inventors have further found that the soil in which these plants are grown has increased organic carbon content relative to soil in which uninoculated plants are grown.

The term "endophytic" relates to a microbe that generally lives within a plant for at least part of its lifecycle, often due to the microbe being able to grow inward into plant tissues in finger-like projections from a superficial site of origin. These fungi can infiltrate plant living tissues for at least a portion of the fungal life cycle often without causing any apparent diseases or harm to the plant that is a native host, in that they are generally not pathogenic to their native hosts. It would be understood that the one or more fungal genus, species or strains of the methods described herein can exist during some portion of the fungal life cycle within the roots of a plant host as an endophyte and in other parts of its life cycle within the soil and will typically alternate or cycle between a root endophytic phase and a free-living soil phase.

Though some endophytic fungi are known for enriching the organic carbon in the soil, each fungal species will generally behave differently when associated with different, and/or non-native plant hosts and/or soil environments and will stabilize the organic carbon with different efficiency.

In some embodiments, the one or more fungal species has a nuclear ribosomal internal transcribed spacer 2(ITS2) sequence that is at least 90% identical, typically at least 91%, least 92%, at least 93%, at least 94%, at least 95%, at least 96%, at least 97%, at least 98%, or at least 99% identical, more typically 100% identical, with the nucleotide sequence of SEQ ID No: 1, 2, 3, 4, 5, 6, 7, 8, 9, 10, 11, 12, 13, 14, 15, 16, 17, 18, or 19.

The terms "identical" or "% identical," in the context of two or more nucleic acids refers to two or more sequences that are the same or have a specified percentage of nucleotides that are the same (i.e., 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/, or the like).

Algorithms for determining % identity are known in the art. An example of an algorithm that is suitable for determining percent sequence identity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information.

Crop Plants

A "plant" means any plant of economic importance and includes cereals (such as wheat, barley, rye, triticale, millet, oats), maize (corn), cotton, soya bean, rice, potatoes, sunflowers, beans, coffee, beets (e.g. sugar beets and fodder beets), peanuts, oilseed rape, poppies, olives, coconuts, cacao, sugar cane, tobacco, vegetables (such as tomatoes, cucumbers, onions and lettuce), lawn and ornamental plants. In a preferred embodiment, the plant is a crop plant. "Crop plant" generally means any cultivated plant that is grown to produce a harvested horticultural product that is grown for sale and/or profit, as well as subsistence crops which may be grown to support other agricultural products, such as livestock. The crop plant may be any crop plant of agronomic importance which is cultivated for food, animal feed, fiber, fuel, and/or industrial purposes. The crop plant may vary from region to region worldwide, wherein the variance may depend on factors such as dietary requirements and environmental conditions.

The methods described herein result in enhanced yield of crop plants. It would be understood these benefits include increased yields.

An "increase in yield" of a crop plant treated with the one or more fungal species includes an increase in fruit, grain or vegetative tissue production of the treated plant relative to that of a crop plant that is the same but which has not been treated with the one or more fungal species described herein when the treated and untreated plant are grown under the same growing conditions. An "untreated control plant" as used herein is a plant grown in a similar soil type under similar conditions (e.g., fertilizer application, watering, etc.) except that no fungal strain is applied to the plant. For example, an increase in yield of a treated wheat plant is an increase in the number and/or weight of wheat grains produced by the treated wheat plant relative to that of an untreated wheat plant grown under the same growth conditions. Typically, the increase in yield of a plant treated with the one or more fungal species is an increase in fruit, grain or vegetative tissue production of the treated plant relative to that of a healthy plant of the same type that has not been treated with the one or more fungal species described herein when the treated and untreated plant are grown under the same growing conditions. A healthy plant is a plant that is not infected with, or affected by, a plant pathogen. Typically, a healthy plant is a plant that is not infected with, or affected by, a plant pathogen, and which is grown under conditions for normal growth of that plant (e.g., is not under stress, such as nutrient or drought stress), such as, for example, the conditions under which the crop plant would be grown under during commercial crop production.

Increased yield in plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, chlorophyll content, nodulation, internode number and distance, root growth (e.g., root number, root length, root mass, root volume), shoot growth (e.g., shoot mass, leaf area, leaf number, plant height) seed size, fruit size, pod size, pod or ear number, seed number per pod or ear, seed mass, enhanced seed filling, reduced seed dispersal, reduced pod dehiscence and lodging resistance. As used herein, "agronomic benefits" means improving one or more of these factors thereby increasing the yield of the plant.

The crop plant may, for example, be one or more compatible crops selected from the group consisting of species of the genus *Triticum, Glycine, Brassica, Gossypium, Zea, Corchorus, Saccharum, Medicago, Lolium, Coffea, Camellia, Oryza, Hordeum, Boehmeria, Nicotiana, Cannabis*, oilseeds, grain legumes, vegetables, fruits, and/or combinations or hybrids thereof. It is contemplated that the list of the crop plants disclosed herein are mere examples for the skilled persons to understand the present disclosure. The crop plants may further include new future species and breeds as well as hybrids produced by grafting or transgenic species.

In preferred embodiments of the invention, the crop plant may, for example, be one or more crops selected from the group consisting of the species *Triticum aestivum, Brassica napus, Brassica rapa, Brassica juncea, Gossypium hirsutum, Gossypium barbadense, Gossypium arboretum, Gossypium Herbaceum, Zea mays, Medicago sativa, Lolium multiflorum, Corchorus capsularis, Saccharum officinarum, Cannabis sativa, Coffea Arabica, Coffea Robusta, Camellia sinensis, Oryza sativa, Hordeum vulgare, Boehmeria nivea* and *Nicotiana tabacum*.

In one embodiment, the crop plant is a cereal plant. Cereal plants include, for example, wheat, rice, corn (maize), rye, oats, barley, sorghum, and some of the millets. In various embodiments, the crop plant is a cereal plant selected from the group consisting of wheat, rice and corn.

In another embodiment, the crop plant is a fibre plant. Fibre plants include, for example, flax, hemp, jute, and cotton. In various embodiments, the crop plant is a fibre plant that is cotton.

In one embodiment, the crop plant is a legume. Legume plants include, for example, soybeans, alfalfa, clover, peanuts, lentils, lupins, peas, and chickpea. In various embodiments, the crop plant is a legume that is soybeans.

In embodiments of the invention, the plant is a "non-native" plant host of the fungal strain. "Non-native" plant host means that the fungi are heterologous to said plant insofar as the fungal strain was collected from a host other than said crop plant.

Endophytic fungi are known to have preferred hosts and growth conditions, and will not necessarily flourish, and therefore will not produce the desired stable SOC, in the absence of their typical growth environment or an association with their native hosts. Moreover, when considering the survival of the fungi in non-native plant hosts, it is difficult to anticipate whether the fungi will prove to be pathogenic to the non-native host. Therefore, fungal species may not readily be compatible with a non-native crop plant host.

Inoculation

As used herein, the terms "inoculate," "apply," "treat," and "deploy" are used interchangeably as are their associated nouns (i.e., "inoculation, "application," "treatment," and "deployment"). The inoculation of the plant with the one or more fungal species may be achieved by any suitable means such as direct addition to the soil and/or plant roots and/or to soil proximal to plant roots, or may be achieved by an initial fungal inoculation of any propagation material, seeds, seedlings and/or immature plants of the crop plant prior to placement of the seed, seedling or immature plant in the soil within which the plant will grow. The inoculation of the one or more fungal species may also be achieved by direct addition to a cultivated soil prior to sowing seeds or planting seedlings that are coated or partially coated with one or more fungal species such that the fungi will become associated with, or grow proximal to, or grow into the roots of a crop plant as the crop matures.

By means of the inoculation, the fungi are deliberately encouraged to become established in the soil and/or grow proximal to, or grow into the roots of a plant (i.e., become associated with) that is a crop plant, wherein it would be understood the fungi may exist and grow in the soil or exist within the plant, or in both simultaneously. In aspects of the invention wherein the treatments or methods rely on the inoculation of a plant with a fungus, it would be understood the fungus need only be associated with the plant for parts of the fungus' lifecycle and that the fungus may survive in the soil in the absence of a plant host or host crop plant.

In other embodiments, the inoculation may be considered a semi-permanent inoculation to a plot of soil that is cultivated, such that the fungus is deployed to said plot of soil and is retained by the soil as the crops are rotated, even in the absence of crops for periods of time.

In some embodiments, the soil is inoculated with the one or more fungal species. The soil may be inoculated with the one or more fungal species prior to planting the plant, for example before, during, or after tilling the soil in preparation for planting. In other embodiments, the soil may be inoculated with the one or more fungal species after the plant has been planted. In some embodiment, the soil is inoculated with the one or more fungal species by planting in the soil plants that have been inoculated with the one or more fungal species.

In some embodiments, the step of inoculating a crop plant comprises applying the one or more fungal species to seeds of the plant prior to planting.

In some embodiments, the step of inoculating a crop plant comprises applying the one or more fungal species to seedlings of the plant.

In some embodiments, the step of inoculating soil comprises deploying the one or more fungal species to a plot of soil that is cultivated, such that the fungus is retained by the soil as the crops are rotated, even in the absence of crops for periods of time.

In one embodiment, the plants are inoculated with one or more fungal species as a seed coating before, during or after one or more of the stages of germination of a seed, or as a root inoculant of a seedling. For example, the treatment may be applied as a seed coating to seeds en masse prior to sowing a crop.

The one or more fungal species for inoculation may be in any suitable form, including, for example, as hyphae, mycelia, conidia and/or combinations thereof. In general, the one or more fungal species for inoculating the plant will be in a form that is substantially free of contaminating microorganisms, with the exception that additional desirable microbes may be added for additional benefits.

In one aspect, there is provided a soil for increasing yield of a crop plant, the soil comprising one or more fungal species from at least one genus selected from *Acrocalymma, Clonostachys, Leptodontidium, Periconia, Phaeosphaeria, Thozetella*, and *Trichoderma*.

In some embodiments, the inoculant may be in the form of a dried powder, a spray, a slurry, a sachet, a liquid, a jelly, a seed coating, an enhancer, and/or combinations thereof.

In some embodiments, the inoculant is in the form of a seed coating, a foliar spray, granule, powder, soil drench or a root dip.

In one embodiment, the inoculant is in the form of a seed coating.

In one embodiment, the inoculant is in the form of a foliar spray.

In one embodiment, the inoculant is in the form of a root dip.

In one embodiment, the inoculant is a granule.

In one embodiment, the inoculant is a powder.

In one embodiment, the composition is a soil drench.

In some embodiments, the one or more fungal species are compatible with commonly used agricultural fungicides. "Compatible" means the one or more fungal species in the treatment is not killed or substantially inhibited (growth or germination or otherwise) by the fungicide, thereby allowing the fungi in the treatment to flourish while restricting the growth of undesirable fungal strains that may have a deleterious effect on the soil, the proximal crops or plants, and/or the level of carbon sequestration and stable carbon production. The fungicide may be any synthetic or natural compound that has a fungistatic or fungicidal function and are commonly used in agriculture. Based on their mode of action, they may kill the fungi or inhibit the germination of fungal spores.

The composition and/or inoculant may comprise suitable solid or liquid carriers and/or adhesive agents.

Suitable solid carriers include mineral earths (e.g., calcium phosphate, calk, clay, diatomaceous earth, dolomite, kaolin, silicates, silica gels, talc, etc), cellulose, and starch. Suitable liquid carriers include water, or any other liquid solvents which are not toxic to the fungus or the plant.

The composition may be prepared in a known manner, by mixing it with customary adjuvants, such as, for example, customary extenders and also solvents or diluents, colorants, wetters, dispersants, emulsifiers, antifoams, preservatives, secondary thickeners, stickers, and also water.

Colorants which may be present in a seed-dressing composition which can be used in accordance with the invention include all colorants which are customary for such purposes. In this context it is possible to use not only pigments, which are of low solubility in water, but also water-soluble dyes. Examples include the colorants known under the designations Rhodamine B, C.I. Pigment Red 112 and C.I. Solvent Red 1.

Wetters that may be present in the seed-dressing composition include all of the substances which promote wetting and which are customary in the formulation of active agrochemical ingredients. Use may be made preferably of alkylnaphthalenesulphonates, such as diisopropyl- or diisobutyl-naphthalenesulphonates.

Dispersants and/or emulsifiers which may be present in the seed-dressing composition include all of the nonionic, anionic and cationic dispersants that are customary in the formulation of active agrochemical ingredients. Use may be made preferably of nonionic or anionic dispersants or of mixtures of nonionic or anionic dispersants. Suitable nonionic dispersants are, in particular, ethylene oxide-propylene oxide block polymers, alkylphenol polyglycol ethers and also tristryrylphenol polyglycol ethers, and the phosphated or sulphated derivatives of these. Suitable anionic dispersants are, in particular, lignosulphonates, salts of polyacrylic acid, and arylsulphonate-formaldehyde condensates.

Antifoams which may be present in the seed-dressing composition include all of the foam inhibitors that are customary in the formulation of active agrochemical ingredients. Use may be made preferably of silicone antifoams and magnesium stearate.

Preservatives which may be present in the seed-dressing composition include all of the substances which can be employed for such purposes in agrochemical compositions. Examples include dichlorophen and benzyl alcohol hemiformal.

Secondary thickeners which may be present in the seed-dressing composition include all substances which can be used for such purposes in agrochemical compositions. Those contemplated with preference include cellulose derivatives, acrylic acid derivatives, xanthan, modified clays and highly disperse silica.

Stickers which may be present in the seed-dressing composition include all customary binders which can be used in seed-dressing products. Preferred mention may be made of polyvinylpyrrolidone, polyvinyl acetate, polyvinyl alcohol and tylose.

In certain aspects, a fungal strain is applied with one or more plants selected from List 1: wheat, rice, corn (maize), rye, oats, barley, sorghum, millet, flax, hemp, jute, cotton, soybeans, alfalfa, clover, peanuts, lentils, lupins, peas, and chickpea.

In one aspect, a fungal strain of the genus *Acrocalymma* is applied to one or more plants selected from List 1. In another aspect, a fungal strain of the genus *Clonostachys* is applied to one or more plants selected from List 1. In another aspect, a fungal strain of the genus *Leptodontidium* is applied to one or more plants selected from List 1. In another aspect, a fungal strain of the genus *Periconia* is applied to one or more plants selected from List 1. In another aspect, a fungal strain of the genus *Phaeosphaeria* is applied to one or more plants selected from List 1. In another aspect, a fungal strain of the genus *Thozetella* is applied to one or more plants selected from List 1. In another aspect, a fungal strain of the genus *Trichoderma* is applied to one or more plants selected from List 1.

In another aspect, a fungal strain of the species *Trichoderma hamatum* is applied to one or more plants selected from List 1. In another aspect, a fungal strain of the species *Periconia macrospinosa* is applied to one or more plants selected from List 1. In another aspect, a fungal strain of the species *Clonostachys rosea* is applied to one or more plants selected from List 1. In another aspect, a fungal strain of the species *Acrocalymma vagum* is applied to one or more plants selected from List 1. In another aspect, a fungal strain of the species *Leptodontidium orchidicola* is applied to one or more plants selected from List 1. In another aspect, a fungal strain of the species *Phaeosphaeria luctuosa* is applied to one or more plants selected from List 1. In another aspect, a fungal strain of the species *Phaeosphaeria vagans* is applied to one or more plants selected from List 1. In another aspect, a fungal strain of the species *Thozetella nivea* is applied to one or more plants selected from List 1. In another aspect, a fungal strain of the species *Trichoderma longipile* is applied to one or more plants selected from List 1. In another aspect, a fungal strain of the species *Trichoderma spirale* is applied to one or more plants selected from List 1.

Soil Organic Carbon

The fungi used in the methods described herein will generally be capable of sequestering and fixing carbon from atmospheric carbon dioxide and converting this carbon to complex polysaccharides for storage as stable carbon in the soil. The sequestered and fixed carbon may also be converted and stored as a stable carbon source by the fungi in the fungi itself as, for example, melanin, chitin, lignin, suberin and carotenoid compounds, or the fungi may exude these compounds to increase the stable carbon in the soil. The deployed fungal endophyte may also convert simple polysaccharide exudate from a host plant into complex polysaccharides for storage as stable carbon in the soil, or within the fungi itself. Lastly, the stability of organic carbon may be enhanced in soil with more stable soil aggregates.

The methods and treatments of the present invention may increase the overall levels of carbon in the soil, but even in cases where overall carbon remains the same or is only slightly increased, it would be understood that the levels of stable carbon in the soil may be increased due to the production and exudation in the soil of complex polysaccharides by the disclosed fungal species.

The fungi may be particularly useful to increase overall levels of carbon in the soil and/or levels of stable carbon in the soil where the soil has a soil organic carbon (SOC) level below a particular threshold. In some aspects, the threshold is a SOC level below 5%, 4%, 3%, 2%, 1%, 0.9%, 0.8%, 0.7%, 0.6%, 0.5%, 0.4%, 0.3%, 0.2%, or 0.1%.

The increase in overall soil carbon and stable soil carbon of a soil that is subjected to the treatments and/or methods of the present disclosure compared to an untreated control (i.e., a "non-inoculated control soil") may be quantified by any methods known to those skilled in the art. The control would be a similar soil sample that had not been exposed to a endophytic fungus as claimed herein (i.e., a fungus had not been deployed in the soil or associated with a plant that had been cultivated in said soil). "Similar soil sample" means that the soil would be from a proximal area with a similar climate and, if the soil had been cultivated, the control sample would have been cultivated by the same plant as the test soil.

In one embodiment, an increase in soil organic carbon is an increase in stable carbon. An increase in the sequestration of atmospheric carbon for storage as stable carbon in the soil, and increasing the levels of stable carbon in the soil, is an increase relative to the amount of sequestration of atmospheric carbon for storage as stable carbon in the soil, and levels of stable carbon in the soil, produced by a plant that has not been treated with the methods of the present disclosure.

Application of the fungi to the plant and/or soil may have one or more desirable effects on the soil and/or associated crops cultivated in the treated soil, including for example, sequestering atmospheric carbon for storage as stable carbon in the soil; and/or increasing the levels of stabilised carbon in the soil.

The inoculation of the soil and/or plants with the fungi may have simultaneous beneficial effects on the soil. For example, sequestration of atmospheric carbon by endophytic fungi as described herein can lead to an increase in the complex polysaccharides in the soil resulting in long-term storage of sequestered atmospheric carbon in a stable form.

Soil organic carbon is the overall soil carbon content of a soil and may be also generally referred to as total organic carbon (TOC) (the terms may be used interchangeably), and this refers only to the carbon component of the organic matter in the soil. However, fluctuations in soil organic carbon may not necessarily correlate to the same fluctuations in stable soil carbon. Indeed, soils subjected to the treatments and methods may demonstrate minimal increases in TOC, but the percentage of said TOC that is captured in a stable form in the soil or in the fungi proliferating in the soil (i.e., complex polysaccharides, melanin, chitin, lignin, suberin and carotenoid compounds) may increase. The skilled addressee would also understand that changes in TOC and stable carbon in soil as a result of the treatments and methods of the present may take weeks, months or years, and therefore appropriate measurement timeframes must be applied. In one embodiment, the increase in soil organic carbon in a soil comprises an increase in stable carbon in the soil.

The soil carbon may be measured by methods including, but not limited to, dry combustion or elemental tests that may be analysed using, for example, the LECO method, and loss on ignition (LOI) tests that may be analysed using the Walkley-Black method (see, for example, Walkley A, and Black IA (1934) An examination of the Degtjareff method for determining soil organic matter, and a proposed modification of the chromic acid titration method. *Soil Science* 37, 29-38.). To assess the prevalence of different types of carbon on the TOC (i.e. to measure the stable, or "recalcitrant" organic carbon), methods may be employed to fractionate to TOC by, for example, measuring soil respiration or the bulk density of the soil.

In embodiments of the invention, the fungal inoculation of soil and/or the plant results in an increase in soil aggregate stability. The increase in soil aggregate stability, or soil aggregation per se, of a soil that is subjected to the treatments and/or methods described herein compared to a control may be quantified by any methods known to those skilled in the art. The control would be a similar soil sample that had not been exposed to the relevant fungus (i.e., a fungus had not been deployed in the soil or associated with a plant that had been cultivated in said soil). "Similar soil sample" means that the soil would be from a proximal area with a similar climate and, if the soil had been cultivated, the control sample would have been cultivated by the same plant as the test soil. The soil aggregate stability may be quantified by measurements compared to controls such as, but not limited to, soil mean weight diameter (MWD), geometric mean diameter (GMD), fractal dimension (D), percentage of aggregates destruction (PAD) and water-stable aggregates stability rate (WSAR). An increase in the MWD, GMD, WSAR and D values are indicative of an increase in soil aggregate stability, while a decrease in PAD value is indicative of an increase in soil aggregate stability.

In various embodiments of the invention, the fungal inoculation may have one or more desirable effects on the soil and/or associated crop plants cultivated in the treated soil, including, but not limited to, sequestering atmospheric carbon for storage as stable carbon in the soil; providing agronomic benefits to the crop plants; increasing the levels of stabilised carbon in the soil used to cultivate the crop plants; and/or increasing the soil aggregate stability of the soil used to cultivate crop plants. In other embodiments of the invention, the fungal inoculation may have two or more of the aforementioned desirable effects on the soil and/or associated crop plants cultivated in the treated soil, or three or more of the aforementioned desirable effects on the soil and/or associated crop plants cultivated in the treated soil.

That the fungal inoculation of the methods of the invention may have numerous, simultaneous effects on the soil and/or associated crop plants cultivated in the treated soil is, in part, possible because some of the desirable effects contribute to other desirable effects. For example, increasing soil aggregate stability is related to the enhanced (and/or longer-term) storage of sequestered atmospheric carbon as well as providing agronomic benefits to said crop plants by virtue of stably aggregated soil being more productive through, for example, improved water retention. In another example, sequestration of atmospheric carbon by the melanised fungi as described herein can lead to an increase in the complex polysaccharides in the soil resulting in long-term storage of sequestered atmospheric carbon in a stable form.

Deposited Fungal Strains

Biological deposits of each of the fungal strains listed in Table 1 were made on the dates shown at the American Type Culture Collection (ATCC®), located at 10801 University Blvd., Manassas, VA 20110, USA, or the National Measurement Institute (NMI), 1/153 Bertie Street, Port Melbourne, Victoria 3207, Australia, under the provisions of the Budapest Treaty and assigned by each International Depositary Authority (IDA) the accession numbers indicated. Upon issuance of a patent, all restrictions upon the deposits will be irrevocably removed. The deposits are intended to meet the requirements of 37 CFR §§ 1.801-1.809. The deposits will be maintained in the IDAs for a period of 30 years, or 5 years after the last request, or for the effective, enforceable life of the patent, whichever is longer, and will be replaced, if necessary, during that period; and the requirements of 37 CFR §§ 1.801-1.809 are met.

TABLE 1

| Strain Number | Species | IDA | Date of Deposit | Accession No. |
|---|---|---|---|---|
| DMTR-CTR-US-73 | Trichoderma hamatum | ATCC | 4 May 2022 | PTA-127301 |
| DMTR-CTR-US-125 | Periconia macrospinosa | ATCC | 4 May 2022 | PTA-127300 |
| DMTR-CTR-US-173 | Clonostachys rosea | ATCC | 4 May 2022 | PTA-127299 |
| DMTR-CTR-11556 | Acrocalymma vagum | NMI | 30 Mar. 2022 | V22/006357 |
| DMTR-CTR-1081 | Clonostachys rosea | NMI | 18 Feb. 2022 | V22/003495 |
| DMTR-CTR-4873 | Leptodontidium orchidicola | NMI | 18 Feb. 2022 | V22/003497 |
| DMTR-CTR-1852 | Periconia macrospinosa | NMI | 30 Mar. 2022 | V22/006358 |
| DMTR-CTR-6649 | Periconia sp. | NMI | 30 Mar. 2022 | V22/006356 |
| DMTR-CTR-3044 | Phaeosphaeria luctuosa/vagans | NMI | 30 Mar. 2022 | V22/006355 |
| DMTR-CTR-2359 | Thozetella nivea | NMI | 18 Feb. 2022 | V22/003496 |
| DMTR-CTR-1291 | Trichoderma longipile/spirale | NMI | 30 Mar. 2022 | V22/006354 |

It would be understood that fungal strains from the same species as those described herein would have similar desirable attributes and are encompassed by the treatments and methods of the present invention.

As used herein, the term "effective amount" means a sufficient quantity of a substance (e.g. fungus) to promote an increase in soil carbon and/or yield of a plant. This term is not to be construed to limit the disclosure to a specific quantity, e.g., number of fungal cells; rather the present disclosure encompasses any amount of the one or more fungal species that is sufficient to achieve the stated purpose. The amount of the one or more fungal species should not be so large as to cause adverse effects in the plant. Generally, the amount of the one or more fungal species may be varied with the way in which the fungi are applied (e.g., to the soil, to the seed or to the seedling) and can be determined by a person skilled in the art.

Throughout the specification and claims, unless the context requires otherwise, the term "substantially" or "about" will be understood to not be limited to the value for the range qualified by the terms. For example, the term "about" may include a range that is ±5%, ±2.5% or ±1% of the value to which the term is applied.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

All headings are for the convenience of the reader and should not be used to limit the meaning of the text that follows the heading, unless so specified.

The present invention is further illustrated by the following examples that should not be construed as limiting. The contents of all references, patents, and published patent applications cited throughout this application, as well as the Figures, are incorporated herein by reference in their entirety for all purposes. In order to exemplify the nature of the present invention such that it may be more clearly understood, the following non-limiting examples are provided.

EXAMPLES

Example 1—Isolations and Characterisation of Fungal Strains

Strains of fungus were isolated from roots of healthy plants and tested for pathogenicity towards various crop plants. Examples of non-pathogenic strains were selected as representatives of various species, and further tested. Additional commercially available strains, KZ399SG (*Periconia macrospinosa*) and LIM1023el (*Periconia macrospinosa*) have been included in some experiments as controls and for support.

Examples of non-pathogenic strains of fungal species used in these studies are listed in Table 2.

TABLE 2

| SEQ ID No. | Strain number | Species | ITS2 sequence |
|---|---|---|---|
| 1 | DMTR-CTR-11556 | Acrocalymma vagum | GCATCGATGAAGAACGCAGCGAAATGCGATAAGTAG TGTGAATTGCAGAATTCAGTGAATCATCGAATCTTTG AACGCACATTGCGCCCCTTGGTATTCCATGGGGCATG CCTGTTCGAGCGTCATTTGAACCCTCAAGCTCTGCTTG GTGTTGGGTGTTTGTCCCGCCATTGCGCGTGGACTCG CCTTAAAGCAATTGGCAGCCATGTAATCCGGCTTTGA GCGCAGCACATTGCGTACTCTCTACTGGGACATGGGC ATCCAGAAGCCTTATTTTTTACTCTTGACCTGGATCA GGTAGGGATACCCGCTGAACTTAAGCATATCAATAAG CGGAGGA |
| 2 | DMTR-CTR-4715 | Acrocalymma vagum | GCATCGATGAAGAACGCAGCGAAATGCGATAAGTAG TGTGAATTGCAGAATTCAGTGAATCATCGAATCTTTG AACGCACATTGCGCCCCTTGGTATTCCATGGGGCATG CCTGTTCGAGCGTCATTTGAACCCTCAAGCTCTGCTTG GTGTTGGGTGTTTGTCCCGCCATTGCGCGTGGACTCG CCTTAAAGCAATTGGCAGCCATGTAATCCGGCTTTGA GCGCAGCACATTGCGTACTCTCTACTGGGACATGGGC ATCCAGAAGCCTTATTTTTTACTCTTGACCTGGATCA GGTAGGGATACCCGCTGAACTTAAGCATATCAATAAG CGGAGGA |

TABLE 2-continued

| SEQ ID No. | Strain number | Species | ITS2 sequence |
|---|---|---|---|
| 3 | DMTR-CTR-1081 | *Clonostachys rosea* | GCATCGATGAAGAACGCAGCGAAATGCGATAAGTAA<br>TGTGAATTGCAGAATTCAGTGAATCATCGAATCTTTG<br>AACGCACATTGCGCCCGCCAGTATTCTGGCGGGCATG<br>CCTGTCTGAGCGTCATTTCAACCCTCATGCCCCTAGGG<br>CGTGGTGTTGGGGATCGGCCAAAGCCCGCGAgGGGAC<br>GGCCGGCCCCTAAATCTAGTGGCGGACCCGTCGTGG<br>CCTCCTCTGCGAAGTAGTGATATTCCGCATCGGAGAG<br>CGACGAGCCCCTGCCGTTAAACCCCCAACTTTCCAAG<br>GTTGACCTCAGATCAGGTAGGAATACCCGCTGAACTT<br>AAGCATATCAATAAGCGGAGGA |
| 4 | DMTR-CTR-US-173 | *Clonostachys rosea* | GCATCGATGAAGAACGCAGCGAAATGCGATAAGTAA<br>TGTGAATTGCAGAATTCAGTGAATCATCGAATCTTTG<br>AACGCACATTGCGCCCGCCAGTATTCTGGCGGGCATG<br>CCTGTCTGAGCGTCATTTCAACCCTCATGCCCCTAGGG<br>CGTGGTGTTGGGGATCGGCCAAAGCCCGCGAGGGAC<br>GGCCGGCCCCTAAATCTAGTGGGGGACCCGTCGTGG<br>CCTCCTCTGCGAAGTAGTGATATTCCGCATCGGAGAG<br>CGACGAGCCCCTGCCGTTAAACCCCCAACTTTCCAAG<br>GTTGACCTCAGATCAGGTAGGAATACCCGCTGAACTT<br>AAGCATATCAATAAGCGGAGGA |
| 5 | DMTR-CTR-4873 | *Leptodontidium orchidicola* | GCATCGATGAAGAACGCAGCGAAATGCGATAAGTAA<br>TGTGAATTGCAGAATTCAGTGAATCATCGAATCTTTG<br>AACGCACATTGCGCCCTCTGGTATTCCGGGGGCATG<br>CCTGTTCGAGCGTCATTATAACCACTCAAGCTCTCGCT<br>TGGTATTGGGGTTCGCGGTTTCGCGGCCCCTAAAATC<br>AGTGGCGGTGCCTGTCGGCTCTACGCGTAGTAATACT<br>CCTCGCGATTGAGTCCGGTAGGTCTACTTGCCAgCAA<br>CCCCTAATTTTTTTAAGGTTGACCTGGATCAGGtAGG<br>GATACCCGCTGAACTTAAGCATATCAATAAGCGGAGG<br>A |
| 6 | DMTR-CTR-US-69 | *Leptodontidium orchidicola* | GCATCGATGAAGAACGCAGCGAAATGCGATAAGTAA<br>TGTGAATTGCAGAATTCAGTGAATCATCGAATCTTTG<br>AACGCACATTGCGCCCTCTGGTATTCCGGGGGCATG<br>CCTGTTCGAGCGTCATTATAACCACTCAAGCTCTCGCT<br>TGGTATTGGGGTTCGCGGTTTCGCGACCCCTAAAATC<br>AGTGGCGGTGCCTGTCGGCTCTACGCGTAGTAATACT<br>CCTCGCGATTGAGTCCGGTAGGTCTACTTGCCAGCAA<br>CCCCTAATTTTTTTAAGGTTGACCTGGATCAGGTAGG<br>GATACCCGCTGAACTTAAGCATATCAATAAGCGGAGG<br>A |
| 7 | DMTR-CTR-1452 | *Periconia macrospinosa* | GCATCGATGAAGAACGCAGCGAAATGCGATAAGTAG<br>TGTGAATTGCAGAATTCAGTGAATCATCGAATCTTTG<br>AACGCACATTGCGGCCATAGGTATTCCTTTGGCCATG<br>CCTGTTCGAGCGTCATTTACACCCTCAAGCCTAGCTTG<br>GTGTTGGGCGTCTGTCCCGCCGTTTTCGCGCGCGGAC<br>TCGCCTCAAAGTCATTGGCGGCGGTCGTGCCGGCCCC<br>CTCGCGCAGCACATTTGCGCTTCTCGGAGGCCCGGCG<br>GATCCGCGCTCCAGCAAGACCTTTCACGACTTGACCT<br>CGGATCAGGTAGGGATACCCGCTGAACTTAAGCATAT<br>CAATAAGCGGAGGA |
| 8 | DMTR-CTR-1850 | *Periconia macrospinosa* | GCATCGATGAAGAACGCAGCGAAATGCGATAAGTAG<br>TGTGAATTGCAGAATTCAGTGAATCATCGAATCTTTG<br>AACGCACATTGCGGCCATAGGTATTCCTTTGGCCATG<br>CCTGTTCGAGCGTCATTTACACCCTCAAGCCTAGCTTG<br>GTGTTGGGCGTCTGTCCCGCCGTTCTCGCGCGCGGAC<br>TCGCCTCAAAGTCATTGGCGGCGGTCGTGCCGGCCCC<br>CTCGCGCAGCACATTTGCGCTTCTCGGAGGCCCGGCG<br>GATCCGCGCTCCAGCAAGAcCTTTCaCGACTTGACCTC<br>GGATCAgGtAGGGATACCCGCTGaACTTAAGCATATC<br>AATAAGCGGAGGA |
| 9 | DMTR-CTR-1852 | *Periconia macrospinosa* | GCATCGATGAAGAACGCAGCGAAATGCGATAAGTAG<br>TGTGAATTGCAGAATTCAGTGAATCATCGAATCTTTG<br>AACGCACATTGCGGCCATAGGGTATTCCTTTGGCCAT<br>GCCTGTTCGAGCGTCATTTACACCCTCAAGCCTAGCTT<br>GGTGTTGGGCGTCTGTCCCGCTTCGCGCGCGGACTCG<br>CCTCAAAGTCATTGGGGGCGGTCGTGCCGGCCCCTGA<br>GCGCAGCACATTTGCGCTTCTCGGAGGCCCGGCGGAc<br>CCGCGCTCCAGCAAGACCTTTCtACGACTTGACCTCGG<br>ATCAGGTAGGGATACCCGCTGAACTTAAGCATATCAA<br>TAAGCGGAGGA |

TABLE 2-continued

| SEQ ID No. | Strain number | Species | ITS2 sequence |
|---|---|---|---|
| 10 | DMTR-CTR-US-122 | *Periconia macrospinosa* | GCATCGATGAAGAACGCAGCGAAATGCGATAAGTAGTGTGAATTGCAGAATTCAGTGAATCATCGAATCTTTGAACGCACATTGCGGCCATAGGTATTCCTTTGGCCATGCCTGTTCGAGCGTCATTTACACCCTCAAGCCTAGCTTGGTGTTGGGCGTCTGTCCCGCCGTTCTCGCGCGCGGACTCGCCTCAAAGTCATTGGCGGCGGTCGTGCCGGCCCCCTCGCGCAGCACATTTGCGCTTCTCGGAGGCCCGGCGGATCCGCGCTCCAGCAAGAcCTTTCaCGACTTGACCTCGGATCA |
| 11 | DMTR-CTR-US-125 | *Periconia macrospinosa* | GCATCGATGAAGAACGCAGCGAAATGCGATAAGTAGTGTGAATTGCAGAATTCAGTGAATCATCGAATCTTTGAACGCACATTGCGGCCATAGGTATTCCTTTGGCCATGCCTGTTCGAGCGTCATTTACACCCTCAAGCCTAGCTTGGTGTTGGGCGTCTGTCCCGCCGTTCTCGCGCGCGGACTCGCCTCAAAGTCATTGGCGGCGGTCGTGCCGGCCCCCTCGCGCAGCACATTTGCGCTTCTCGGAGGCCCGGCGGATCCGCGCTCCAGCAAGACCTTTCaCGACTTGACCTCGGATCAgGtAGGGATACCCGCTgAACTTAAGCATATCAATAAGCGGAGGÅ |
| 12 | DMTR-CTR-6649 | *Periconia sp.* | GCATCGATGAAGAACGCAGCGAAATGCGATAAGTAGTGTGAATTGCAGAATTCAGTGAATCATCGAATCTTTGAACGCACATTGCGGCCATAGGGTATTCCTTTGGCCATGCCTGTTCGAGCGTCATTTACACCCTCAAGCCTAGCTTGGTGTTGGGCGTCTGTCCCGCTTCGCGCGCGGACTCGCCTCAAAGTCATTGGCGGCGGTCGTGCCGGCCCCTGAGCGCAGCACATTTGCGCTTCTCGGAGGCCCGGCGGAcCCGCGCTCCAGCAAGACCTTTCtACGACTTGACCTCGGATCAGGTAGGGATACCCGCTGAACTTAAGCATATCAATAAGCGGAGGA |
| 13 | DMTR-CTR-3044 | *Phaeosphaeria luctuosa/vagans* | GCATCGATGAAGAACGCAGCGAAATGCGATAAGTAGTGTGAATTGCAGAATTCAGTGAATCATCGAATCTTTGAACGCACATTGCGCCCCTTGGTATTCCATGGGGCATGCCTGTTCGAGCGTCATTTGTACCCTCAAGCTCTGCTTGGTGTTGGGTGTTTGTCCTCTCCTTTGCGTTTGGACTCGCCTTAAAGCAATTGGCAGCCAGTGTTTTGGTATTGAAGCGCAGCACATTTTGCGATTCTAGCCGATAATACTTTGCGTCCATAAGCCTTTTTTCACTTTTGACCTCGGaTCAGGTAGGGATACCCGCTGAACTTAAGCATATCAATAAGCGGAGGA |
| 14 | DMTR-CTR-2359 | *Thozetella nivea* | GCATCGATGAAGAACGCAGCGAAATGCGATAAGTAATGTGAATTGCAGAATTCAGTGAATCATCGAATCTTTGAACGCACATTGCGCCCGCCGGTATTCCGGCGGGCATGCCTGTTCGAGCGTCATTTCAACCCTCAGGCCTCGCCTGGTGTTGGGGCTCCTGCGCACTGCAGGCCCTCAAAGGCAGCGGGGGTGCGCCTACGAACCGAACGCAGTAGTTTTCTCTCGTTCTGGTCTCGCGGGCGTGCTCCGGCCGTTAAACCCCCTTTATaTcCAATGGTTGACCTGGATCAGGTAGGAATACCCGCTGAACTTAAGCATATCAATAAGCGGAGGA |
| 15 | DMTR-CTR-US-73 | *Trichoderma hamatum* | GCATCGATGAAGAACGCAGCGAAATGCGATAAGTAATGTGAATTGCAGAATTCAGTGAATCATCGAATCTTTGAACGCACATTGCGCCCGCCAGTATTCTGGGGGGCATGCCTGTCCGAGCGTCATTTCAACCCTCGAACCCCTCCGGGGGATCGGCGTTGGGGATCGGGACCCCTCACCGGGTGCCGGCCCTGAAATACAGTGGCGGTCTCGCCGCAGCCTCTCCTGCGCAGTAGTTTGCACAACTCGCACCGGGAGCGCGGCGCGTCCACGTCCGTAAAACACCCAACTTCTGAAATGTTGACCTCGGATCAGGTAGGAATACCCGCTGAACTTAAGCATATCAATAAGCGGAGGA |
| 16 | DMTR-CTR-US-76 | *Trichoderma koningiopsis* | GCATCGATGAAGAACGCAGCGAAATGCGATAAGTAATGTGAATTGCAGAATTCAGTGAATCATCGAATCTTTGAACGCACATTGCGCCCGCCAGTATTCTGGCGGGCATGCCTGTCCGAGCGTCATTTCAACCCTCGAACCCCTCCGGGGGTCGGCGTTGGGGATCGGGAACCCCTAAGACGGGATCCCGGCCCCGAAATACAGTGGCGGTCTCGCCGCAGCCTCTCCTGCGCAGTAGTTTGCACAACTCGCACCGGGAGCGCGGCGCGTCCACGTCCGTAAAACACCCAACTTCTGAAATGTTGACCTCGGATCAGGTAGGAATACCCGCTGAACTTAAGCATATCAATAAGCGGAGGA |

TABLE 2-continued

| SEQ ID No. | Strain number | Species | ITS2 sequence |
|---|---|---|---|
| 17 | DMTR-CTR-1291 | Trichoderma longipile/spirale | GCATCGATGAAGAACGCAGCGAAATGCGATAAGTAATGTGAATTGCAGAATTCAGTGAATCATCGAATCTTTGAACGCACATTGCGCCCGCCAGTATTCTGGCGGGCATGCCTGTCCGAGCGTCATTTCAACCCTCGAACCCCTCCGGGGGGTCGGCGTTGGGGATCGGCCCTTCACGGGGCCGGCCCCGAAATACAGTGGCGGTCTCGCCGCAGCCTCTCCTGCGCAGTAGTTTGCACACTCGCATCGGGAGCGCGGCGCGTCCATTGCCGTAAAACACCCAACTTTCTGAAATGTTGACCTCGGATCAGGTAGGAATACCCGCTGAACTTAAGCATATCAATAAGCGGAGGA |
| 18 | DMTR-CTR-US-98 | Trichoderma virens | GCATCGATGAAGAACGCAGCGAAATGCGATAAGTAATGTGAATTGCAGAATTCAGTGAATCATCGAATCTTTGAACGCACATTGCGCCCGCCAGTATTCTGGGGGGCATGCCTGTCCGAGCGTCATTTCAACCCTCGAACCCCTCCGGGGGGTCGGCGTTGGGGATCGGCCCTTTACGGGGCCGGCCCCGAAATACAGTGGCGGTCTCGCCGCAGCCTCTCCTGCGCAGTAGTTTGCACACTCGCATCGGGAGCGCGGCGCGTCCACAGCCGTTAAACACCCCAAACTTCTGAAATGTTGACCTCGGATCAGGTAGGAATACCCGCTGAACTTAAGCATATCAATAAGCGGAGGA |
| 19 | DMTR-CTR-US-78 | Trichoderma viride | GCATCGATGAAGAACGCAGCGAAATGCGATAAGTAATGTGAATTGCAGAATTCAGTGAATCATCGAATCTTTGAACGCACATTGCGCCCGCCAGTATTCTGGGGGGCATGCCTGTCCGAGCGTCATTTCAACCCTCGAACCCCTCCGGGGGTCCGGCGTTGGGGATCGGGAACCCCTAAGACGGGATCCCGGCCCCGAAATACAGTGGCGGTCTCGCCGCAGCCTCTCCTGCGCAGTAGTTTGCACAACTCGCACCGGGAGCGCGGCGCGTCCACGTCCGTAAAACACCCAACTTCTGAAATGTTGACCTCGGATCAGGTAGGAATACCCGCTGAACTTAAGCATATCAATAAGCGGAGGA |

Example 2—Treatment of Germinated Wheat Seedling with Liquid Cultures of Selected Fungi Materials and Methods As an internal variable and also to ensure successful colonisation of wheat seeds by fungal inoculants, pre-germinated wheat seeds were treated with 3 ml fungal suspension (fungi grown in sterile potato dextrose broth for 7-10 days in a shaking incubator at 150 RPM, 25° C. and total darkness). The plates were incubated at 25° C. in darkness until sowing the following day. Treatments were as shown in Table 3.

TABLE 3

Treatments and combinations used for wheat trial

| Treatment | Isolate ID | Soil type |
|---|---|---|
| T28 | DMTR-CTR-3044 | Non-sterile |
| T29 | DMTR-CTR-1081 | Non-sterile |
| T31 | DMTR-CTR-6649, DMTR-CTR-1081 | Non-sterile |
| T34 | Seedling + Agar plug (Control) | Non-sterile |
| T35 | Soil Only/Unplanted | Non-sterile |

Termination of terminal pots (100 mm): Eight weeks post sowing, the terminal 100 mm pots were harvested for measurement of total carbon in the soil, along with measurement of number of tillers. To confirm the colonisation, tissue samples (roots and shoots) were plated.

Termination of terminal pots (140 mm): Eight weeks post sowing, the terminal 140 mm pots were harvested for measurement of total carbon in the soil, along with measurement of number of tillers. To confirm the colonisation, tissue samples (roots and shoots) were plated.

Collection of cores and soil processing: Soil cores from the terminal pots were collected after the shoots were cut using secateurs. A soil corer was used to core the soil right above the crown region of the harvested shoot, including the roots and the soil. The core was 10 cm deep and about 3 cm wide. The cores were transferred into 50 mL FALCON® tubes and allowed to dry for 48-72 h at 40° C. in the drying oven. The dried soil was homogenised and sieved using a 1.5 mm mesh sieve to remove roots, large clods and clumps from the soil. The samples were processed and sent for carbon analysis at EAL.

Results

Final Carbon: Results for various treatments in non-sterile soil are shown in Table 4.

TABLE 4

| | | Property | | |
|---|---|---|---|---|
| Treatment Number | Isolates | Mean TOC (%) | % Increase over Control | p = 0.00248 Significance Group |
| T28 | DMTR-CTR-3044 | 1.54 | 8.10 | b |
| T35 | Soil Only/Unplanted | 1.53 | 7.63 | b |
| T31 | DMTR-CTR-6649, DMTR-CTR-1081 | 1.51 | 6.46 | bc |
| T29 | DMTR-CTR-1081 | 1.50 | 5.75 | bcd |
| T34 | Control | 1.42 | 0.00 | de |

Soil analysis from the final pots showed that there was a significant increase in carbon for single isolates DMTR-CTR-3044, DMTR-CTR-1081 and consortia:6649-1081 in comparison to the control.

Number of heads: The number of heads were counted. Statistical analysis showed that treatment T10T10 (DMTR-CTR-3044), was significantly different from the control.

DISCUSSION

Significant findings of this trial show changes in TOC which occurs at different stages of plant growth and the increase and decrease at various stages suggests the role of microbial communities in decomposition. These findings also show the need for carbon sequestration as stable aggregates, which is more resistant to microbial decomposition. In addition, comparison of both sterile and non-sterile soil shows the importance of microbial communities and interactions between microbes in both carbon accumulation and decomposition. Other significant findings of the trial show that some non-DSE(s) such as DMTR-CTR-1081 significantly increased TOC in comparison to the control.

Example 3—Evaluation of Fungal Strains with Spring Wheat

Material and Methods

Several fungal strains were used individually and in consortia to evaluate their carbon sequestration capability in soil using two varieties of spring wheat (Shelly and Lang-MN). Additionally, final yields were also measured and compared to the control.

The study was based on a Randomized Complete Block Design with 8 replicates/treatment. 2 varieties of wheat were used with 14 entries for both varieties. The soil was 60% Illinois topsoil, 20% sand and 20% perlite (by volume). Soil was homogenized by mixing and sieved to remove clumps, and stones and to remove plant debris, especially weeds, roots and other visible masses.

Enough seeds to allow 2 seeds per pot (which were thinned back to 1 seedling upon successful germination) were washed repeatedly on a plastic sieve under running tap water to remove all debris and mummies. The clean seeds were surface sterilized by soaking in 2% NaOCl for one minute followed by washing twice for five minutes with sterile reverse osmosis (RO) water to remove any traces of NaOCl. The surface sterilized seeds were transferred to a surface sterilized plastic tray. The sterilized seeds were stored dried prior to planting The inoculation with microbes was performed with a sterile cork borer, which was used to cut 7-10 mm round PDA plugs containing fungal hyphae from the actively growing hyphal edge on a PDA plate. The agar plug was placed into pre-prepared holes in pots, fungi-side-up and 2 of the surface sterilized seeds were placed directly atop of the agar plug.

Once the pots germinated, any pots bearing 2 successfully germinated seeds were thinned back to 1 plant per pot.

Data capture includes the information set out in Table 5.

TABLE 5

| Assessment | Method | Timing |
|---|---|---|
| Germination and Emergence | Count number of emerged plants for each treatment/entry | 14 days after planted |
| Interim carbon soil sampling | Soil cores taken to bottom of pot with corer, halfway between plant and the pot edge. Entire sample sent to Minnesota lab or to lab designated for carbon analysis | Peak vegetative stage, in-line with interim plant height |
| Final carbon soil sampling | Soil cores taken to bottom of pot with corer, halfway between plant and the pot edge. Entire sample sent to Minnesota lab or to lab designated for carbon analysis | Prior to termination |
| Yield (if taken to maturity) | Thresh and weigh | Harvest |

Results

Results are set out in Table 6.

TABLE 6

| | Emergence | | Midterm TOC % | | Midterm TOC % – Δ % Control | | Harvest TOC % | | Harvest TOC % – Δ % Control | | Yield (grams/plant) | | Yield – Δ % Control | |
|---|---|---|---|---|---|---|---|---|---|---|---|---|---|---|
| | \multicolumn{14}{c}{Wheat varieties} |
| | S | LM | S | LM | S | LM | S | LM | S | LM | S | LM | S | LM |
| DMTR-CTR-US-76 | 8 | 8 | 2.80 | 2.60 | 0.54 | -1.71 | 2.89 | 3.01 | 1.12 | 16.13 | 4.56 | 4.33 | -8.97 | -13.71 |
| DMTR-CTR-US-78 | 7 | 8 | 2.92 | 2.67 | 4.72 | 0.75 | 2.67 | 2.80 | -6.54 | 7.33 | 4.86 | 4.64 | -2.96 | -7.50 |
| DMTR-CTR-US-173 | 5 | 8 | 2.84 | 2.77 | 1.65 | 4.70 | 2.78 | 2.57 | -2.55 | -1.42 | 3.67 | 4.72 | -26.62 | -5.98 |
| DMTR-CTR-US-73 | 8 | 8 | 2.90 | 2.75 | 4.02 | 3.80 | 2.84 | 2.83 | -0.50 | 8.49 | 4.80 | 4.32 | -4.07 | -13.88 |
| DMTR-CTR-US-69 | 7 | 8 | 2.79 | 2.67 | -0.25 | 0.81 | 2.77 | 2.77 | -3.52 | 6.38 | 5.58 | 4.32 | 10.63 | -13.91 |
| KZ399SG | 7 | 7 | 2.82 | 2.73 | 1.00 | 2.91 | 2.81 | 2.84 | -1.76 | 8.81 | 5.23 | 5.56 | 4.52 | 10.78 |
| DMTR-CTR-US-173 + DMTR-CTR-US-69 | 8 | 8 | 2.72 | 2.74 | -2.61 | 3.27 | 2.83 | 2.79 | -0.94 | 7.23 | 5.43 | 5.56 | 8.57 | -6.23 |
| Control | 8 | 8 | 2.79 | 2.65 | 0.00 | 0.00 | 2.86 | 2.61 | 0.00 | 0.00 | 5.00 | 5.56 | 0.00 | 0.00 |

S = Shelley;
LM = Lang-MN

SUMMARY

For wheat variety Shelly, germination/emergence of the plants was slightly affected by strains DMTR-CTR-US-78, DMTR-CTR-US-69, and KZ399SG. Strain DMTR-CTR-US-173 had a more severe impact on the germination/emergence. Mid-term soil carbon analysis showed strains DMTR-CTR-US-76, DMTR-CTR-US-78, DMTR-CTR-US-173, DMTR-CTR-US-73, and KZ399SG performed better than the control by having higher total organic carbon.

For the final soil carbon analysis, strains DMTR-CTR-US-76 performed better than the control with higher total organic carbon. For final yield, strains DMTR-CTR-US-69, consortia DMTR-CTR-US-173+ DMTR-CTR-US-69 and KZ399SG showed increased seed weight per plant compared to the control.

These results suggest that strains DMTR-CTR-US-69 and KZ399SG have the potential of increasing soil total organic carbon and final yield for this variety.

For wheat variety Lang-MN, germination/emergence of the plants was only slightly affected by strain KZ399SG. Mid-term soil carbon analysis showed all strains with the exception of DMTR-CTR-US-76 performing better than the control with higher total organic carbon. For the final soil carbon analysis, all strains with the exception of DMTR-CTR-US-173 performed better than the control with higher total organic carbon.

For final yield, treatment KZ399SG showed increased seed weight per plant compared to the control. These results showed strain KZ399SG with the potential of increasing soil total organic carbon and final yield for this variety. All other strains have the potential of increasing Midterm and/or Harvest soil total organic carbon depending on the wheat variety being used.

DISCUSSION

The findings of this experiment suggest that all tested strains have the potential of increasing midterm and/or harvest soil total organic carbon in one or more seed variety and all but DMTR-CTR-US-173 improved final soil carbon levels on the Lang variety. Moreover, the final results suggest that DMTR-CTR-US-69, consortia DMTR-CTR-US-173+DMTR-CTR-US-69 and KZ399SG have the potential to increase final yield for this crop in one or more seed variety tested.

Example 4—Soybean

Background

The soybean has been found associated with several beneficial rhizospheric microorganisms. These microorganisms have also been used to enhance soybean production and plant health, however no studies have been carried out in soybean on the role of endophytic fungi on crop improvement and soil carbon.

In this study, DSE fungal based inoculum in combination with bacterial consortia were deployed to enhance the soil carbon and agronomic features of soy. Fungal inoculants are environmentally-friendly and deliver nutrients to plants more sustainably and can increase the soil quality by enhancing the soil organic carbon. Before going into small plot field trials to test the inoculants, carrying out the experiments under the glasshouse and controlled condition provides an opportunity to screen for the efficacy of the fungal inoculum. Fungi can be a pathogen or beneficial to plants. Glasshouse trials provide the opportunity to look for the promising and negative features of fungi. In the process of developing the inoculum package for soybean, three glasshouse trials were initiated. This trial was run over a period of 3 months.

Material and Methods

Ten fungal strains, including DSEs, as single treatments, and in consortia, were tested in glasshouse conditions using a field soil on soybean plants.

Results

Of the treatments used, twelve treatments showed an overall change in total organic carbon of between −0.2% and 15.5%. The increase was statistically significant in the three best performing strains, with an increase of 15.5%, 14.4% and 11.3% over the control treatment.

Plant height was taken as a marker of growth against control, due to the indeterminate nature of soybean. There was a non-significant variation of between −19% and 27% in plant height below, or above the planted control.

Total organic carbon in soil samples for various treatments is set out in Table 7.

TABLE 7

| Inoculum/Treatment | Increased TOC |
| --- | --- |
| DMTR-CTR-2359 | Yes |
| DMTR-CTR-1291 | Yes |
| DMTR-CTR-4715 | Yes |
| DMTR-CTR-1291, DMTR-CTR-4715 | Yes |

Material and Methods

Surface sterilisation was carried out by washing the seeds twice with and incubated overnight at 25° C. followed by 50% bleach treatment for two minutes, and triple rinsing. Pre germination was carried out prior to planting with seeds surface sterilised and incubated in the fully wet sterile paper towel inside petri dish for two days at 25° C. incubator.

The trial was set up in a randomised block design (RBD), and the treatments were replicated 8 times within the trial. The full formulation/extended treatment was also applied as a soil drench as a different application strategy in addition to the seed coating method.

Growth observations were made throughout the trial, with plant data collected throughout the trial as a proxy for yield data. Soil cores were collected using a consistent protocol prior to harvest and analysed by Environmental Laboratories Australia (EAL), an independent laboratory. Dry combustion for total organic carbon was carried out by EAL, with raw data returned and analysed.

Results

Trial two contained ten individual strains, four consortia with a total sixteen treatments. Interim, plant growth and soil carbon were measured.

TABLE 8

| Interim Soil Carbon - Percentage Difference from Control | |
| --- | --- |
| Inoculum/Treatment | % difference from control |
| DMTR-CTR-2359 | 15.4672392 |
| DMTR-CTR-1291 | 5.692801167 |
| DMTR-CTR-4715 | 2.416756124 |
| Unplanted | 1.568204048 |
| DMTR-CTR-1291, DMTR-CTR-4715 | 0.429641237 |
| Seed + agar | 0 |

Example 5—Wheat, Soy, Cotton and Corn

Greenhouse trials were conducted at 3 different locations: Wisconsin, Illinois and Texas. Four different crops were used: Corn, soy, spring wheat and cotton. For each crop, 2 varieties were used. The objectives of the experiments were to identify strains (individual or consortia) that could sequester more carbon in a recalcitrant form and identify strains (individual or consortia) that could have a positive effect in final yield.

Materials and Methods

Using a sterile cork borer 7-10 mm diameter round PDA plugs containing actively growing hyphae were cut on the edge of plate. The agar plugs were transferred into pre-prepared holes in the pots (~½" deep) with fungi side up. 2 of the surface sterilized seeds were placed directly atop of the agar plug, and the seed and agar plugs were covered with soil and lightly tapped to get good soil-seed contact Results Results are set out in Table 9.

TABLE 9

| Crops | | Corn | Soy | Cotton | Wheat | Measured |
|---|---|---|---|---|---|---|
| Demetrius Codes | Fungi | Percentage differences with Control (differences calculated with each experiment) | | | | Traits |
| DMTR-CTR-US-173 | *Clonostachys rosea* | 1.2 | -2.36 | -0.39 | -0.77 | Harvest TOC |
| | | -7.8 | 9.24 | 6.55 | -12.81 | Yield |
| DMTR-CTR-US-173 + DMTR-CTR-US-69 | *Clonostachys rosea* + *Leptodontidium orchidicola* | -4.94 | -5.01 | 0.34 | 1.44 | Harvest TOC |
| | | -6.97 | 11.39 | -7.8 | -4.78 | Yield |
| DMTR-CTR-US-69 | *Leptodontidium orchidicola* | -7.52 | -0.07 | 4.72 | 2.31 | Harvest TOC |
| | | -15.52 | 10 | 3.6 | -6.77 | Yield |
| DMTR-CTR-US-73 | *Trichoderma hamatum* | 1.91 | -2.22 | 18.2 | 0.16 | Harvest TOC |
| | | -27.6 | 11.34 | 9.1 | -13.37 | Yield |
| DMTR-CTR-US-76 | *Trichoderma koningiopsis* | -0.68 | -2.55 | | 4.84 | Harvest TOC |
| | | -11.64 | 13.3 | | -13.1 | Yield |
| DMTR-CTR-US-78 | *Trichoderma viride* | -0.65 | -1.14 | | -0.54 | Harvest TOC |
| | | -13.03 | 8.27 | | -10.78 | Yield |
| K2399 SG | *Periconia macrospinosa* | | -3.43 | 2.9 | 3.33 | Harvest TOC |
| | | | 26.19 | 10.5 | 7.651 | Yield |
| K2399 SG + DMTR-CTR-US-69 | *Periconia macrospinosa* + *Leptodontidium orchidicola* | | | -0.3 | | Harvest TOC |
| | | | | -26.7 | | Yield |
| LIM1023el | *Periconia macrospinosa* | | | 19 | | Harvest TOC |
| | | | | 9.5 | | Yield |
| LIM1023el + DMTR-CTR-US-173 | *Periconia macrospinosa* + *Clonostachys rosea* | | | 4.9 | | Harvest TOC |
| | | | | -8.2 | | Yield |

Example 6—Soybean

Background

Several fungal strains collected in different parts of the United States were used individually and in consortia to evaluate their carbon sequestration capability in soil. Additionally, final yields were also measured and compared to the control.

Material and Methods

The study was based on a randomised complete block design with 8 replicates/treatment.

Seeds were washed repeatedly on a plastic sieve under running tap water to remove all debris and mummies and surface sterilized by soaking in 2% NaOCl for one minute followed by washing twice for five minutes with sterile reverse osmosis (RO) water to remove any traces of NaOCl.

The seeds were then transferred to a surface sterilized plastic tray and dried by blotting before being inoculated with microbes.

7-10 mm round PDA plugs containing fungal hyphae were cut from the actively growing hyphal edge on a PDA before the agar plugs were placed into pre-prepared holes in pots, fungi-side-up. 2 of the surface sterilized seeds were directly atop of the agar plug.

Once the pots were germinated, any pots bearing 2 successfully germinated seeds were thinned back to 1 plant per pot.

Data capture included the information set out in Table 10.

TABLE 10

| Assessment | Method | Timing |
|---|---|---|
| Germination and Emergence | Count number of emerged plants for each treatment/entry. | 14 days after planted |
| Interim carbon soil sampling | Soil cores taken to bottom of pot with corer, half way between plant and pot edge. Entire sample sent to Soil Carbon Minnesota lab or to lab designated by us for carbon analysis | Peak vegetative stage, in-line with interim plant height |
| Final carbon soil sampling | Soil cores taken to bottom of pot with corer, half way between plant and pot edge. Entire sample sent to Soil Carbon Minnesota lab or lab designated by us for carbon analysis | Prior to termination |
| Yield (if taken to maturity) | Thresh and weigh | Harvest |

Results

Results are shown in Table 11.

TABLE 11

| | Emergence | | Emergence Δ % − Control | | Midterm TOC − Δ % − Control | | Harvest TOC − Δ % − Control | | Yield − Δ % − Control | |
|---|---|---|---|---|---|---|---|---|---|---|
| | | | | | Soy Varieties | | | | | |
| | A3244 | P9273 | A3244 | P9273 | A3244 | P9273 | A3244 | P9273 | A3244 | P9273 |
| DMTR-CTR-US-76 | 8 | 6 | 14.3 | 20 | -4.9 | -3.2 | -1.1 | -5.2 | 27.5 | 9.4 |
| DMTR-CTR-US-78 | 8 | 6 | 14.3 | 20 | -3.3 | -0.1 | 2.5 | -6.2 | -0.8 | 9.4 |
| DMTR-CTR-US-173 | 7 | 6 | 0 | 20 | -5.6 | -1 | -2.2 | -6.9 | 4.1 | 14.2 |
| DMTR-CTR-US-73 | 8 | 6 | 14.3 | 20 | 1.4 | -2 | 2 | -7 | 23.2 | -3.2 |

TABLE 11-continued

|  | Emergence | | Emergence Δ % – Control | | Midterm TOC – Δ % – Control | | Harvest TOC – Δ % – Control | | Yield – Δ % – Control | |
|---|---|---|---|---|---|---|---|---|---|---|
| Soy Varieties | | | | | | | | | | |
|  | A3244 | P9273 | A3244 | P9273 | A3244 | P9273 | A3244 | P9273 | A3244 | P9273 |
| DMTR-CTR-US-173 + DMTR-CTR-US-69 | 8 | 6 | 14.3 | 20 | 0.1 | −4.2 | −4.1 | −6.7 | 24.6 | 7.3 |
| DMTR-CTR-US-69 | 6 | 4 | −14.3 | −20 | −5.7 | 2.8 | −4.1 | −10.2 | 20.2 | 6.9 |
| KZ399SG | 5 | 3 | −28.6 | −40 | −1.1 | −0.9 | −2.4 | −5.2 | 33.3 | 14.3 |
| Control | 7 | 5 | 0 | 0 | 0 | 0 | 0 | 0 | 0.0 | 0.0 |

DISCUSSION

Fungal strains DMTR-CTR-US-73 and DMTR-CTR-US-78 showed potential to increase soil total organic carbon. Moreover, the results suggest that all tested strains had the potential to increase final yield for the tested varieties of this crop.

Example 7—Australian Trials

A total of 184 treatment combinations, comprising 24 fungal strains, including Dark septate endophytes (DSEs), in a statistically designed experimental combination, were tested in glasshouse conditions using agricultural field soil, and soybean plants.

BACKGROUND

In this study, we assessed the dark septate endophytic (DSE) fungal based inoculum in combination with non DSE fungi, and bacterial consortia to enhance the soil carbon and agronomic features of soy.

Fungal inoculants are environmentally friendly and deliver nutrients to plants more sustainably and can increase the soil quality by enhancing the soil organic carbon. Before going into small plot field trials to test the inoculants, carrying out the experiments under the glasshouse and controlled condition provides an opportunity to screen for the efficacy of the fungal inoculum. Fungi can be a pathogen or beneficial to plants. Glasshouse trials provide the opportunity to look for the promising and negative features of fungi. In the process of developing the inoculum package for soybean, glasshouse and field trials were carried out.
Materials and Methods Experimental combinations were created using the Design of experiment (Custom Design) tool in the JMP Pro 14.3. Overall, 184 experimental combinations were tested in this trial based on different fungal inoculum, with and without plant.

All the fungal cultures listed in table 1 were revived from a water culture and incubated on potato dextrose agar (PBA) at 25° C. in a constant temperature room for two weeks. 5 mm agar discs were cut from the periphery of the colony (actively growing cells) using sterile corkborer inside the biosafety cabinet.

Surface sterilisation of the seeds was carried out by washing the seeds twice and incubating the seeds overnight at 25° C. followed by 50% bleach treatment for two minutes, and triple rinsing. Pre germination was carried out prior to planting with seeds surface sterilised and incubated in a fully wet sterile paper towel inside a petri dish for two days in a 25° C. incubator.

Although agronomic characteristics were monitored, emphasis was given to the soil carbon. Soil cores were collected using a consistent protocol prior to harvest and analysed by Environmental Laboratories Australia (EAL), an independent laboratory. Dry combustion for total organic carbon was carried out by EAL, with raw data returned and analysed using MINITAB® Statistical Software.

The glasshouse trials were conducted in Orange NSW, Australia. The glasshouse was not temperature and light controlled. But the temperature and humidity in the glasshouse is constantly monitored. Results are shown in Table 12.

TABLE 12

Soybean Growing in Glasshouse.

| Strain | Organism | Mean Seed Weight | Seed Weight Percent Different from Control | Mean TOC | TOC Percent Different from Control |
|---|---|---|---|---|---|
| DMTR-CTR-4715 | Acrocalymma vagum | 12.65 | 35.15 | 0.89 | 7.23 |
| DMTR-CTR-1081 | Clonostachys rosea | 11.32 | 20.94 | 0.96 | 15.66 |
| DMTR-CTR-4873 | Leptodontidium orchidicola | 14.36 | 53.42 | 1.01 | 21.69 |
| DMTR-CTR-3044 | Phaeosphaeria luctuosa | 10.45 | 11.65 | 0.95 | 14.46 |
| DMTR-CTR-2359 | Thozetella nivea | 12.36 | 32.05 | 0.97 | 16.87 |
| DMTR-CTR-1291 | Trichoderma longipile | 13.56 | 44.87 | 0.92 | 10.84 |
| Planted Control | Planted Control | 9.36 | 0.00 | 0.83 | 0.00 |
| Unplanted Control | Unplanted Control |  |  | 0.67 | −19.27 |

Based on the glasshouse data, strains that increased TOC in the soil, and these were chosen for further analysis in the agricultural field for plant benefit in terms of yield increase.
Field Trials Strains of fungal species were initially screened in the laboratory for the ability to sequester carbon as described above. A selection of strains that showed potential for carbon sequestration, were trialled in field conditions. Two field trials were carried out for all the strains that showed better performance in terms of carbon accumulation in the glasshouse experiments. Two trials were carried out in order to assess the beneficial qualities of the endophytic fungal inoculants in varying agro-ecological zones. One trial was carried out in Coleambally, NSW while the other one at Jacobs Well, Queensland.

Material and Methods

For each strain (see Table 14), 10 mL of liquid fungal formulation, 1 mL of *Rhizobium* and 6 mL of sticker per Kg of soybean seed. For the treatment comprising 1 strain (such as Treatment 3), mix 10 mL liquid formulation, 1 mL of *Rhizobium* and 6 mL sticker per 1 Kg of soybean seed. For a treatment comprising 2 strains (such as Treatment 15), a total of 20 mL liquid formulation (10 mL of each strain), mL of *Rhizobium* and 12 mL of sticker (6 mL per strain) need to be mixed per Kg of seed. The actual amount of liquid formulation and sticker required for seed treatment is calculated based on the actual amount of seed to be treated using the above-mentioned application rate. Seeds were planted using the soybean mechanical planter. All the treatments were planted on the same day. Plants were constantly monitored and standard nutrient regime for the soybean was followed.

TABLE 13

| Treatment Number | Treatment Description |
|---|---|
| 1 | Soil only (no plant, no fungal strain) |
| 2 | Plant only (no fungal strain) + Rhizobium |
| 3 | DMTR-CTR-4715 + Rhizobium |
| 4 | DMTR-CTR-1291 + Rhizobium |
| 5 | DMTR-CTR-3044 + Rhizobium |
| 6 | DMTR-CTR-4873 + Rhizobium |
| 7 | DMTR-CTR-1081 + Rhizobium |
| 8 | DMTR-CTR-2359 + Rhizobium |
| 9 | DMTR-CTR-2359 + DMTR-CTR-1081 + Rhizobium |
| 10 | DMTR-CTR-4873 + DMTR-CTR-1291 + Rhizobium |
| 11 | DMTR-CTR-2359 + DMTR-CTR-4873 + Rhizobium |
| 12 | DMTR-CTR-4873 + DMTR-CTR-1081 + Rhizobium |

After a hundred days of growth grains were harvested. Each plot was harvested using a mechanical plot harvester Haldrup or Kingaroy Engineering works (KEW). Weight of the grains was recorded in terms of yield per plot (t/ha).

Soils were sampled on all plots using the hand corer. For each plot, 15 cm core was collected from 3 random paints within each plot. All the soils were combined in the same plastic bag. Using the hand corer, core down to 15 cm (be consistent, mark 15 cm line on corer). Samples were taken from half-way between 2 plants, on the row, not in-between rows and by avoiding the edge rows. Soils Samples were sent immediately to the laboratory for analysing the TOC and the results are shown in Tables 14 and 15.

TABLE 14

Coleambally

| Strain ID | Organisms | Harvest Mean Yield (t/ha) | Significance Group | % Increase over Control |
|---|---|---|---|---|
| DMTR-CTR-1291 | Trichoderma longipile | 1.2 | a | 71.4 |
| DMTR-CTR-2359 + DMTR-CTR-4873 | Thozetella nivea + Leptodontidium orchidicola | 1.1 | ab | 57.1 |
| DMTR-CTR-2359 | Thozetella nivea | 0.9 | ab | 28.6 |
| DMTR-CTR-4873 + DMTR-CTR-1291 | Leptodontidium orchidicola + Trichoderma longipile | 0.9 | ab | 28.6 |
| DMTR-CTR-4715 | Acrocalymma vagum | 0.8 | ab | 14.3 |
| DMTR-CTR-3044 | Phaeosphaeria luctuosa | 0.8 | ab | 14.3 |
| DMTR-CTR-1081 | Clonostachys rosea | 0.8 | ab | 14.3 |
| DMTR-CTR-2359 + DMTR-CTR-1081 | Thozetella nivea + Clonostachys rosea | 0.8 | ab | 14.29 |

TABLE 14-continued

Coleambally

| Strain ID | Organisms | Harvest Mean Yield (t/ha) | Significance Group | % Increase over Control |
|---|---|---|---|---|
| Control (Planted) | Control | 0.7 | ab | Control |
| DMTR-CTR-4873 | Leptodontidium orchidicola | 0.7 | ab | 0.0 |
| DMTR-CTR-4873 + DMTR-CTR-1081 | Leptodontidium orchidicola + Clonostachys rosea | 0.7 | ab | 0.0 |
| Negative control (No plant) | Negative control | 0.0 | c | No Plant |

TABLE 15

Jacobs Well

| Strain ID | Organisms | Harvest Mean Yield (t/ha) | Significance group | % increase over control |
|---|---|---|---|---|
| DMTR-CTR-4873 + DMTR-CTR-1291 | Leptodontidium orchidicola + Trichoderma longipile | 3.03 | a | 53.52 |
| DMTR-CTR-4873 | Leptodontidium orchidicola | 3.01 | a | 52.82 |
| DMTR-CTR-1291 | Trichoderma longipile | 2.92 | a | 47.89 |
| DMTR-CTR-2359 + DMTR-CTR-1081 | Thozetella nivea + Clonostachys rosea | 2.90 | a | 47.18 |
| DMTR-CTR-3044 | Phaeosphaeria luctuosa | 2.88 | a | 45.77 |
| DMTR-CTR-4715 | Acrocalymma vagum | 2.75 | a | 39.44 |
| DMTR-CTR-4873 + DMTR-CTR-1081 | Leptodontidium orchidicola + Clonostachys rosea | 2.71 | a | 37.32 |
| DMTR-CTR-1081 | Clonostachys rosea | 2.68 | a | 35.92 |
| DMTR-CTR-2359 | Thozetella nivea | 2.65 | ab | 34.51 |
| DMTR-CTR-2359 + DMTR-CTR-4873 | Thozetella nivea + Leptodontidium orchidicola | 2.61 | ab | 32.39 |
| Control (Planted) | Control | 1.97 | b | Control |
| Negative control (No plant) | Negative control | 0.00 | c | No plant |

Example 8—US Trials

Background

Fungal strains collected in different parts of the United States were used individually and in consortia to evaluate their carbon sequestration capability in soil. Additionally, final yields were also measured and compared to the control.

Material and Methods

The study was based on a randomised complete block design with 8 replicates/treatment.

Seeds were washed repeatedly on a plastic sieve under running tap water to remove all debris and mummies and surface sterilized by soaking in 2% NaOCl for one minute followed by washing twice for five minutes with sterile RO water to remove any traces of NaOCl.

The seeds were then transferred to a surface sterilized plastic tray and dried by blotting before being inoculated with microbes.

7-10 mm round PDA plugs containing fungal hyphae were cut from the actively growing hyphal edge on a PDA before the agar plugs were placed into pre-prepared holes in pots, fungi-side-up. 2 of the surface sterilized seeds were directly atop of the agar plug.

Once the pots were germinated, any pots bearing 2 successfully germinated seeds were thinned back to 1 plant per pot.

Data capture included the information set out in Table 16.

TABLE 16

| Assessment | Method | Timing |
|---|---|---|
| Germination and Emergence | Count number of emerged plants for each treatment/entry. | 14 days after planted |
| Interim carbon soil sampling | Soil cores taken to bottom of pot with corer, half way between plant and pot edge. Entire sample sent to Soil Carbon Minnesota lab or to lab designated by us for carbon analysis | Peak vegetative stage, in-line with interim plant height |
| Final carbon soil sampling | Soil cores taken to bottom of pot with corer, half way between plant and pot edge. Entire sample sent to Soil Carbon Minnesota lab or lab designated by us for carbon analysis | Prior to termination |
| Yield (if taken to maturity) | Thresh and weigh | Harvest |

Results

Results are shown in Table 17

TABLE 17

| Location | Crop | Treatment | Species | Yield (g/plant) | Yield - Δ % - Control |
|---|---|---|---|---|---|
| Wisconsin | Soybean | Control | | 15.1 | 0.0 |
| Wisconsin | Soybean | DMTR-CTR-US-76 | Trichoderma koningiopsis | 17.3 | 14.8 |
| Wisconsin | Soybean | DMTR-CTR-US-173 + DMTR-CTR-US-69 | Consortium | 17.8 | 17.7 |
| Wisconsin | Soybean | DMTR-CTR-US-69 | Leptodontidium orchidicola | 17.9 | 18.5 |
| Wisconsin | Soybean | DMTR-CTR-US-173 | Clonostachys rosea | 18.3 | 21.0 |
| Wisconsin | Soybean | DMTR-CTR-US-73 | Trichoderma hamatum | 18.6 | 23.3 |
| Wisconsin | Soybean | DMTR-CTR-US-78 | Trichoderma viride | 18.8 | 24.7 |

DISCUSSION

Fungal strains DMTR-CTR-US-76, DMTR-CTR-US-78, DMTR-CTR-US-173, and consortia of DMTR-CTR-US-173+DMTR-CTR-US-69 showed potential to increase soil total organic carbon. Moreover, the results suggest that all tested strains had the potential to increase final yield for the tested seed of this crop.

Example 9—Stable Carbon

Background

A preliminary experiment using fungal strains DMTR-CTR-1852 (*Periconia macrospinosa*) was performed to determine if the strains was capable of increasing the percentage of stable carbon in the soil, even in the event the percentage of total carbon is not increased.

Materials and Methods

The experiment was performed in a pot with red soil in winter with consistent light. Triplicate soil cores were taken for carbon analysis just above where the plant shoot was cut off, as well as from the bulk of the pot.

Results

Total carbon in the "rhizosphere" increased for DMTR-CTR-1852 with a 16.8% increase compared to the control, but there was no total carbon increase in the total soil.

Higher stability of Carbon in AggC (aggregate carbon) and overall more recalcitrant AggC was present with DMTR-CTR-1852.

The higher MAOM (mineral associated organic matter carbon) for the DMTR-CTR-1852 isolate is likely due to an increase in rhizodeposition due to the presence of the fungi.

Example 10—Fractionation of MAOM

Two field trials were carried out in Bundaberg, Queensland to assess the Carbon sequestration capacity of a number of fungal strains Soybean seed was inoculated with sufficient quantity of fungi by means of a liquid seed treatment. Treatments were planted on the same day. Plants were constantly monitored and a standard nutrient regime for the soybean was followed. After a hundred days of growth, grains were harvested.

Soils were sampled on all plots using a hand corer. For each plot, 15 cm cores were collected from 3 random points within each plot and subjected to fractionation. Soil fractionation analysis was carried out as per Buss et al (2021). In short, soil samples were disaggregated, followed by wet sieving and density separation of AggC (aggregate carbon), POC (particulate organic matter carbon) and MAOM (mineral associated organic matter carbon). Fractions were dried, weighed and total carbon was measured by combustion using the LECO® carbon analyser model C832.

Results are shown in Table 18. Each of the treatments increased AggC, MAOM, and total carbon in the soil compared to the untreated controls.

TABLE 18

| Treatment | POM | AggC | MAOM | total C (sum) | POM | AggC | MAOM | total C (sum) |
|---|---|---|---|---|---|---|---|---|
| | | C (% soil) | | | | C (% increase over control) | | |
| Unplanted and uninoculated | 0.027 | 1.019 | 0.900 | 1.945 | | | | |
| Planted but uninoculated | 0.041 | 1.013 | 0.750 | 1.805 | | | | |
| *Trichoderma longipile* 1291 | 0.048 | 1.291 | 0.947 | 2.286 | 16% | 27% | 26% | 27% |
| *Clonostachys rosea* 1081 | 0.031 | 1.035 | 0.796 | 1.862 | −25% | 2% | 6% | 3% |
| *Leptodontidium orchidicola* 4873 | 0.040 | 1.341 | 0.772 | 2.153 | −4% | 32% | 3% | 19% |
| *Thozetella nivea* 2359 | 0.024 | 1.188 | 0.759 | 1.972 | −41% | 17% | 1% | 9% |

Example 11—Corn Field Trials with *P. macrospinosa* DMTR-CTR-US-125

BACKGROUND

To evaluate the effects of *Periconia macrospinosa* DMTR-CTR-US-125 on soil carbon and crop yield, two independent corn field trials were conducted in Clinton and Boone Counties, Indiana, USA, with loam soil and in Armstrong County, Texas, USA, with clay loam soil.

Materials and Methods

*Periconia macrospinosa* DMTR-CTR-US-125 was applied directly to corn seed immediately prior to sowing with a carrier. Control corn seed were treated only with the carrier. Four or five replicates were included for each treatment. The average total organic carbon (TOC) and average grain yield in each treatment group were determined at harvest.

For TOC measurement, representative soil samples were chemically treated with acid to remove all forms of carbonate (inorganic carbon) and leave the organic component. The carbon of the processed sample was quantitatively determined using a resistance furnace for combustion. The sample was ignited in an oxygen rich combustion chamber at 1350° C. An aliquot of the combustion gas was then passed through an infrared absorption detector for carbon measurement.

Results

Results for TOC and crop yield are shown in Tables 19 and 20, respectively.

TABLE 19

| Treatment | Trial Location | TOC (%) | Change Compared to Control |
|---|---|---|---|
| Untreated Control | Indiana | 0.9512 | — |
| DMTR-CTR-US-125 | Indiana | 1.0628 | +11.73% |
| Untreated Control | Texas | 1.0684 | — |
| DMTR-CTR-US-125 | Texas | 1.0854 | +1.59% |

TABLE 20

| Treatment | Trial Location | Yield (bu/acre) | Change Compared to Control |
|---|---|---|---|
| Untreated Control | Indiana | 150.5 | — |
| DMTR-CTR-US-125 | Indiana | 164.9 | +9.57% |
| Untreated Control | Texas | 144.3 | — |
| DMTR-CTR-US-125 | Texas | 157.4 | +9.06% |

*Periconia macrospinosa* DMTR-CTR-US-125 improved TOC and grain yield in both field trials.

Example 12—Soy Greenhouse Trials with *P. macrospinosa* DMTR-CTR-US-125

Background

To evaluate the effects of *Periconia macrospinosa* DMTR-CTR-US-125 on soil carbon and crop yield, a greenhouse trial with Soy Variety ASGROW® 3244 was conducted with soy plants grown in Black Loam Mix, which is a loam soil.

Materials and Methods

*Periconia macrospinosa* DMTR-CTR-US-125 was applied directly to soy seed immediately prior to sowing with a carrier. Control corn seed were treated only with the carrier. Six replicates were included for each treatment. The average total organic carbon (TOC) and average yield in each treatment group were determined at harvest. TOC measurements were performed as outlined in Example 11.

Results

Results for TOC and crop yield are shown in Tables 21 and 22, respectively.

TABLE 21

| Treatment | TOC (%) | Change Compared to Control |
|---|---|---|
| Untreated Control | 4.5507 | — |
| DMTR-CTR-US-125 | 4.5998 | +1.08% |

TABLE 22

| Treatment | Yield (bu/acre) | Change Compared to Control |
|---|---|---|
| Untreated Control | 13.77 | — |
| DMTR-CTR-US-125 | 16.30 | +18.37% |

*Periconia macrospinosa* DMTR-CTR-US-125 improved both TOC and soy yield.

Example 13—Cotton Field Trial with *P. macrospinosa* DMTR-CTR-US-125

Background

To evaluate the effects of *Periconia macrospinosa* DMTR-CTR-US-125 on crop yield, a cotton field trial was conducted in Donley County, Texas, USA, with clay loam soil.

Materials and Methods

*Periconia macrospinosa* DMTR-CTR-US-125 was applied directly to cotton seed immediately prior to sowing with a carrier. Control cotton seed were treated only with the carrier. Five replicates were included for each treatment. The average lint yield in each treatment group was determined at harvest.

Results

Results for crop yield are shown in Tables 23.

TABLE 23

| Treatment | Yield (lb/acre) | Change Compared to Control |
|---|---|---|
| Untreated Control | 1239.0 | — |
| DMTR-CTR-US-125 | 1320.0 | +6.54% |

*Periconia macrospinosa* DMTR-CTR-US-125 markedly improved cotton yield in this field trial.

Example 14—Barley Field Trials with *P. macrospinosa* DMTR-CTR-1852

Background

To evaluate the effects of *Periconia macrospinosa* DMTR-CTR-1852 on soil carbon and crop yield, two independent barley field trials were conducted in Canowindra, New South Wales, Australia and in Perth, Western Australia, Australia.

Materials and Methods

*Periconia macrospinosa* DMTR-CTR-US-1852 was applied directly to barley seed immediately prior to sowing with a carrier. Untreated barley seed were sown as a control. Six replicates were included for each treatment. The average total organic carbon (TOC) and average yield in each treatment group were determined at harvest. TOC measurements were performed with either a HONE CARBON® sensor using spectroscopy or a LECO® instrument using combustion of carbon.

Results

Results for TOC and crop yield are shown in Tables 24 and 25, respectively.

TABLE 24

| Treatment | Trial Location | TOC (%) | Change Compared to Control |
|---|---|---|---|
| Untreated Control | Canowindra | 0.98 | — |
| DMTR-CTR-1852 | Canowindra | 1.03 | +5.1% |
| Untreated Control | Perth | 1.81 | — |
| DMTR-CTR-1852 | Perth | 1.91 | +5.5% |

TABLE 25

| Treatment | Trial Location | Yield (T/Ha) | Change Compared to Control |
|---|---|---|---|
| Untreated Control | Canowindra | 4.1 | — |
| DMTR-CTR-1852 | Canowindra | 4.2 | +2.4% |
| Untreated Control | Perth | 2.9 | — |
| DMTR-CTR-1852 | Perth | 3.0 | +3.4% |

*Periconia macrospinosa* DMTR-CTR-1852 improved TOC and yield in both field trials.

Example 15—Lupin Bean Field Trial with *P. macrospinosa* DMTR-CTR-1852

Background

To evaluate the effects of *Periconia macrospinosa* DMTR-CTR-1852 on soil carbon and crop yield, a lupin bean field trial was conducted in Young, New South Wales, Australia.

Materials and Methods

*Periconia macrospinosa* DMTR-CTR-US-1852 was applied directly to lupin bean seed immediately prior to sowing with a carrier. Untreated lupin bean seed were sown as a control. Six replicates were included for each treatment. The average total organic carbon (TOC) and average yield in each treatment group were determined at harvest. TOC measurements were performed with either a HONE CARBON® sensor using spectroscopy or a LECO® instrument using combustion of carbon.

Results

Results for TOC and crop yield are shown in Tables 26 and 27, respectively.

TABLE 26

| Treatment | TOC (%) | Change Compared to Control |
|---|---|---|
| Untreated Control | 1.15 | — |
| DMTR-CTR-1852 | 1.27 | +10.4% |

TABLE 27

| Treatment | Yield (T/Ha) | Change Compared to Control |
|---|---|---|
| Untreated Control | 3.51 | — |
| DMTR-CTR-1852 | 3.66 | +4.3% |

*Periconia macrospinosa* DMTR-CTR-1852 improved both TOC and yield in the lupin bean field trial.

Example 16—Chickpea Field Trial with *P. macrospinosa* DMTR-CTR-1852

Background

To evaluate the effects of *Periconia macrospinosa* DMTR-CTR-1852 on soil carbon and crop yield, a chickpea field trial was conducted in Wagga Wagga, New South Wales, Australia.

Materials and Methods

*Periconia macrospinosa* DMTR-CTR-US-1852 was applied directly to chickpea seed immediately prior to sowing with a carrier. Untreated chickpea seed were sown as a control. Six replicates were included for each treatment. The average total organic carbon (TOC) and average yield in each treatment group were determined at harvest. TOC measurements were performed with either a HONE CARBON® sensor using spectroscopy or a LECO® instrument using combustion of carbon.

Results

Results for TOC and crop yield are shown in Tables 28 and 29, respectively.

TABLE 28

| Treatment | TOC (%) | Change Compared to Control |
|---|---|---|
| Untreated Control | 1.46 | — |
| DMTR-CTR-1852 | 1.50 | +2.7% |

TABLE 29

| Treatment | Yield (T/Ha) | Change Compared to Control |
|---|---|---|
| Untreated Control | 1.175 | — |
| DMTR-CTR-1852 | 1.229 | +4.6% |

*Periconia macrospinosa* DMTR-CTR-1852 improved both TOC and yield in the chickpea field trial.

Example 17—Barley Field Trials with *A. vagum* DMTR-CTR-11556

Background

To evaluate the effects of *Acrocalymma vagum* DMTR-CTR-11556 on soil carbon and crop yield, two independent barley field trials were conducted in Canowindra, New South Wales, Australia and in Corowa, New South Wales, Australia.

Materials and Methods

*Acrocalymma vagum* DMTR-CTR-11556 was applied directly to barley seed immediately prior to sowing with a carrier. Untreated barley seed were sown as a control. Six replicates were included for each treatment. The average total organic carbon (TOC) and average yield in each treatment group were determined at harvest. TOC measurements were performed with either a HONE CARBON® sensor using spectroscopy or a LECO® instrument using combustion of carbon.

Results

Results for TOC and crop yield are shown in Tables 30 and 31, respectively.

TABLE 30

| Treatment | Trial Location | TOC (%) | Change Compared to Control |
|---|---|---|---|
| Untreated Control | Canowindra | 0.98 | — |
| DMTR-CTR-11556 | Canowindra | 1.18 | +20.4% |
| Untreated Control | Corowa | 3.23 | — |
| DMTR-CTR-11556 | Corowa | 3.26 | +0.9% |

TABLE 31

| Treatment | Trial Location | Yield (T/Ha) | Change Compared to Control |
|---|---|---|---|
| Untreated Control | Canowindra | 4.10 | — |
| DMTR-CTR-11556 | Canowindra | 4.37 | +6.6% |
| Untreated Control | Corowa | 2.5 | — |
| DMTR-CTR-11556 | Corowa | 2.9 | +16.0% |

*Acrocalymma vagum* DMTR-CTR-11556 improved TOC and yield in both field trials.

Example 18—Canola Field Trial with *A. vagum* DMTR-CTR-11556

Background

To evaluate the effects of *Acrocalymma vagum* DMTR-CTR-1155 on crop yield, a canola field trial was conducted in Perth, Western Australia, Australia.

Materials and Methods

*Acrocalymma vagum* DMTR-CTR-1155 was applied directly to canola seed immediately prior to sowing with a carrier. Untreated canola seed were sown as a control. Six replicates were included for each treatment. The average yield in each treatment group was determined at harvest.

Results

Results for crop yield are shown in Tables 32.

TABLE 32

| Treatment | Yield (T/Ha) | Change Compared to Control |
|---|---|---|
| Untreated Control | 1.30 | — |
| DMTR-CTR-11556 | 1.42 | +9.2% |

*Acrocalymma vagum* DMTR-CTR-1155 markedly improved canola yield in this field trial.

Example 19—Barley Field Trials with *Periconia* sp. DMTR-CTR-6649

Background

To evaluate the effects of *Periconia* sp. DMTR-CTR-6649 on soil carbon and crop yield, two independent barley field trials were conducted in Canowindra, New South Wales, Australia and in Corowa, New South Wales, Australia.

Materials and Methods

*Periconia* sp. DMTR-CTR-6649 was applied directly to barley seed immediately prior to sowing with a carrier. Untreated barley seed were sown as a control. Six replicates were included for each treatment. The average total organic carbon (TOC) and average yield in each treatment group were determined at harvest. TOC measurements were performed with either a HONE CARBON® sensor using spectroscopy or a LECO® instrument using combustion of carbon.

Results

Results for TOC and crop yield are shown in Tables 33 and 34, respectively.

TABLE 33

| Treatment | Trial Location | TOC (%) | Change Compared to Control |
|---|---|---|---|
| Untreated Control | Canowindra | 1.01 | — |
| DMTR-CTR-6649 | Canowindra | 1.10 | +8.9% |
| Untreated Control | Corowa | 1.96 | — |
| DMTR-CTR-6649 | Corowa | 2.05 | +4.6% |

TABLE 34

| Treatment | Trial Location | Yield (T/Ha) | Change Compared to Control |
|---|---|---|---|
| Untreated Control | Canowindra | 4.10 | — |
| DMTR-CTR-6649 | Canowindra | 4.33 | +5.6% |
| Untreated Control | Corowa | 2.5 | — |
| DMTR-CTR-6649 | Corowa | 2.6 | +4.0% |

*Acrocalymma vagum* DMTR-CTR-11556 improved TOC and yield in both field trials.

Example 20—Canola Field Trials with *Periconia* sp. DMTR-CTR-6649

Background

To evaluate the effects of *Periconia* sp. DMTR-CTR-6649 on soil carbon and crop yield, a canola field trial were conducted in Canowindra, New South Wales, Australia.
Materials and Methods
*Periconia* sp. DMTR-CTR-6649 was applied directly to canola seed immediately prior to sowing with a carrier. Untreated canola seed were sown as a control. Six replicates were included for each treatment. The average total organic carbon (TOC) and average yield in each treatment group were determined at harvest. TOC measurements were performed with either a HONE CARBON® sensor using spectroscopy or a LECO® instrument using combustion of carbon.
Results
Results for TOC and crop yield are shown in Tables 35 and 36, respectively.

TABLE 35

| Treatment | TOC (%) | Change Compared to Control |
|---|---|---|
| Untreated Control | 1.25 | — |
| DMTR-CTR-6649 | 1.35 | +8.0% |

TABLE 36

| Treatment | Yield (T/Ha) | Change Compared to Control |
|---|---|---|
| Untreated Control | 2.22 | — |
| DMTR-CTR-6649 | 2.26 | +1.8% |

*Acrocalymma vagum* DMTR-CTR-11556 improved TOC and yield in the canola field trial.

Example 21—Corn Field Trial with *T. hamatum* DMTR-CTR-US-73

Background

To evaluate the effects of *Trichoderma hamatum* DMTR-CTR-US-73 on soil carbon and crop yield, a corn field trial was conducted in Renville County, Minnesota, USA, with clay loam soil.
Materials and Methods
*Trichoderma hamatum* DMTR-CTR-US-73 was applied directly to corn seed immediately prior to sowing with a carrier. Control corn seed were treated only with the carrier. Five replicates were included for each treatment. The average total organic carbon (TOC) and average grain yield in each treatment group were determined at harvest.

For TOC measurement, representative soil samples were chemically treated with acid to remove all forms of carbonate (inorganic carbon) and leave the organic component. The carbon of the processed sample was quantitatively determined using a resistance furnace for combustion. The sample was ignited in an oxygen rich combustion chamber at 1350° C. An aliquot of the combustion gas was then passed through an infrared absorption detector for carbon measurement.
Results
Results for TOC and crop yield are shown in Tables 37 and 38, respectively.

TABLE 37

| Treatment | TOC (%) | Change Compared to Control |
|---|---|---|
| Untreated Control | 1.710 | — |
| DMTR-CTR-US-73 | 2.380 | +39.2% |

TABLE 38

| Treatment | Yield (bu/acre) | Change Compared to Control |
|---|---|---|
| Untreated Control | 164.12 | — |
| DMTR-CTR-US-73 | 165.60 | +0.9% |

*Trichoderma hamatum* DMTR-CTR-US-73 improved TOC and grain yield in the corn field trial.

Example 22—Corn Field Trial with *C. rosea* DMTR-CTR-US-173

Background

To evaluate the effects of *Clonostachys rosea* DMTR-CTR-US-173 on soil carbon and crop yield, a corn field trial was conducted in Clinton and Boone Counties, Indiana, USA, with clay loam soil.
Materials and Methods
*Clonostachys rosea* DMTR-CTR-US-173 was applied directly to corn seed immediately prior to sowing with a carrier. Control corn seed were treated only with the carrier. Four replicates were included for each treatment. The average total organic carbon (TOC) and average grain yield in each treatment group were determined at harvest.
For TOC measurement, representative soil samples were chemically treated with acid to remove all forms of carbonate (inorganic carbon) and leave the organic component. The carbon of the processed sample was quantitatively determined using a resistance furnace for combustion. The sample was ignited in an oxygen rich combustion chamber at 1350° C. An aliquot of the combustion gas was then passed through an infrared absorption detector for carbon measurement.
Results
Results for TOC and crop yield are shown in Tables 38 and 39, respectively.

TABLE 38

| Treatment | TOC (%) | Change Compared to Control |
|---|---|---|
| Untreated Control | 0.9512 | — |
| DMTR-CTR-US-173 | 1.101 | +15.7% |

TABLE 39

| Treatment | Yield (bu/acre) | Change Compared to Control |
| --- | --- | --- |
| Untreated Control | 150.50 | — |
| DMTR-CTR-US-173 | 173.42 | +15.2% |

*Clonostachys rosea* DMTR-CTR-US-173 improved TOC and grain yield in the corn field trial.

Example 23—Soybean Glasshouse Experiment

Background

To evaluate the effects of *Thozetella nivea* DMTR-CTR-2359, *Leptodontidium orchidicola* DMTR-CTR-4873, and *Trichoderma longipile* DMTR-CTR-1291 on various aspects of soybean plant health and growth, a glasshouse trial was conducted in Canberra, Australia.

Materials and Methods

The Hayman soybean variety was used. Seed were surface sterilized with bleach and then rinsed with sterile water. River loam soil was purchased from a commercial supplier in Canberra and used for all soybean plants. The river loam soil has the characteristics shown in Table 40.

TABLE 40

| Parameter | Experimental Soil |
| --- | --- |
| Soluble Calcium (mg/kg) | 1,881 |
| Soluble Magnesium (mg/kg) | 319 |
| Soluble Potassium (mg/kg) | 512 |
| Soluble Phosphorus (mg/kg) | 17 |
| Nitrate Nitrogen (mg/kg N) | 76 |
| Ammonium Nitrogen (mg/kg N) | 3.6 |
| Sulphur (mg/kg S) | 34 |
| pH | 7.90 |
| Electrical Conductivity (dS/m) | 0.595 |
| Estimated Organic Matter (% OM) | 4.0 |
| Exchangeable Calcium (mg/kg) | 1,927 |
| Exchangeable Magnesium (mg/kg) | 323 |
| Exchangeable Potassium (mg/kg) | 775 |
| Exchangeable Sodium (mg/kg) | 310 |
| Exchangeable Aluminium (mg/kg) | 2.29 |
| Exchangeable Hydrogen (mg/kg) | <1 |
| Effective Cation Exchange Capacity (ECEC) (cmol$_+$/kg) | 16 |
| Calcium (%) | 62 |
| Magnesium (%) | 17 |
| Potassium (%) | 13 |
| Sodium - ESP (%) | 8.6 |
| Aluminium (%) | 0.16 |
| Hydrogen (%) | 0.00 |
| Calcium/Magnesium Ratio | 3.6 |
| Zinc (mg/kg) | 7.0 |
| Manganese (mg/kg) | 20 |
| Iron (mg/kg) | 67 |
| Copper (mg/kg) | 1.4 |
| Boron (mg/kg) | 0.58 |
| Silicon (mg/kg Si) | 37 |
| Total Carbon (%) | 2.3 |
| Total Nitrogen (%) | 0.20 |
| Carbon/Nitrogen Ratio | 12 |
| Basic Texture | Clay Loam/River loam |
| Basic Colour | Brownish |
| Chloride Estimate (equiv. mg/kg) | 381 |

All the fungal cultures were revived from stored water cultures and incubated at a 25° C. constant temperature for two weeks. 5 mm agar discs were cut from the periphery of the colony (actively growing cells) using a sterile cork borer and the fungal inoculums were raised by solid-state fermentation. Fungal inoculums were applied at a dose of E3 (1×), E5 (2×), and E9 (3×). Rhizobial inoculums contained *Bradyrhizobium japonicum* and were applied at the dose of E5 per seed. Each treatment was applied with ten replicates. Treatments and dose rates are outlined in Table 41.

TABLE 41

| Treatment | Strains | Dose Rate |
| --- | --- | --- |
| UTC | Untreated Control | — |
| T3 | DMTR-CTR-4873 | 1X |
| T4 | DMTR-CTR-4873 | 2X |
| T5 | DMTR-CTR-4873 | 3X |
| T6 | DMTR-CTR-2359 | 1X |
| T7 | DMTR-CTR-2359 | 2X |
| T8 | DMTR-CTR-2359 | 3X |
| T9 | DMTR-CTR-1291 | 1X |
| T10 | DMTR-CTR-1291 | 2X |

Results

Plant Phenotypes

Visual plant phenotype and health observations were made throughout the trial. FIG. 1 shows a representative phenotype of the untreated control (un-inoculated) and *Leptodontidium orchidicola* DMTR-CTR-4873 inoculated plants. A severe growth retardation and chlorosis (yellowing) was observed throughout all untreated control plants (i.e., control: inoculated with *rhizobium* but no fungal inoculation application). However, the pots/plants inoculated with *rhizobium* and fungal isolates were observed as healthy, green and with increased height.

Figure 2:
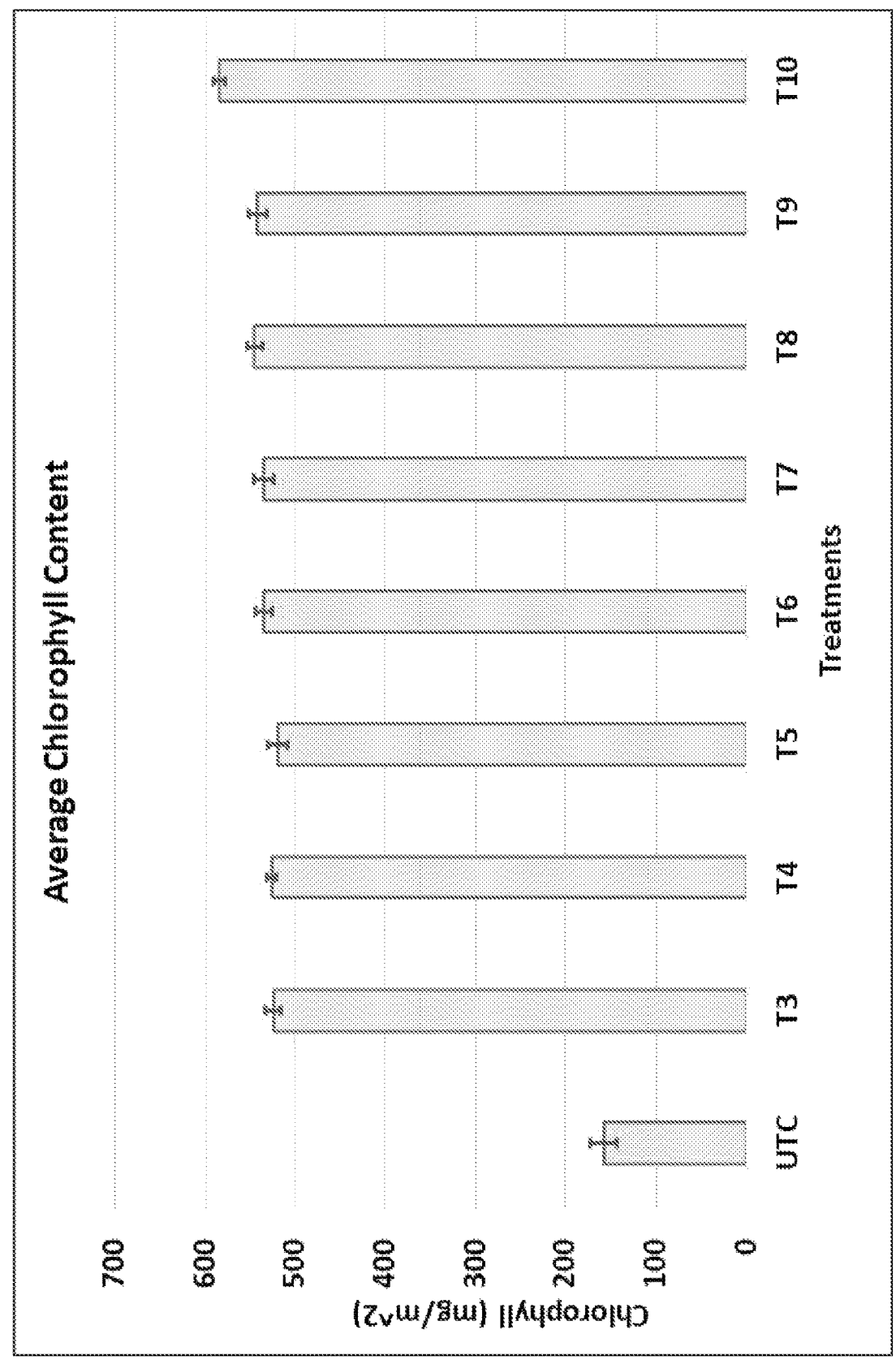
FIG. 2 depicts total chlorophyll content from untreated control (UTC) and treated soy plants inoculated with different concentrations of fungal cultures. Error bars indicate standard error (SE).

Total Chlorophyll 6-8 weeks post inoculation, chlorophyll content was measured from the untreated control and fungal inoculated plants. To measure the chlorophyll, three observations were taken from each leaf and three leaves were observed per plant. All the chlorophyll readings were taken using a CCM 300 chlorophyll content meter. FIG. 2 shows the increased amount of chlorophyll in treated plants as compared to the untreated control plants.

Plant Health and Height Observations

Figure 3:
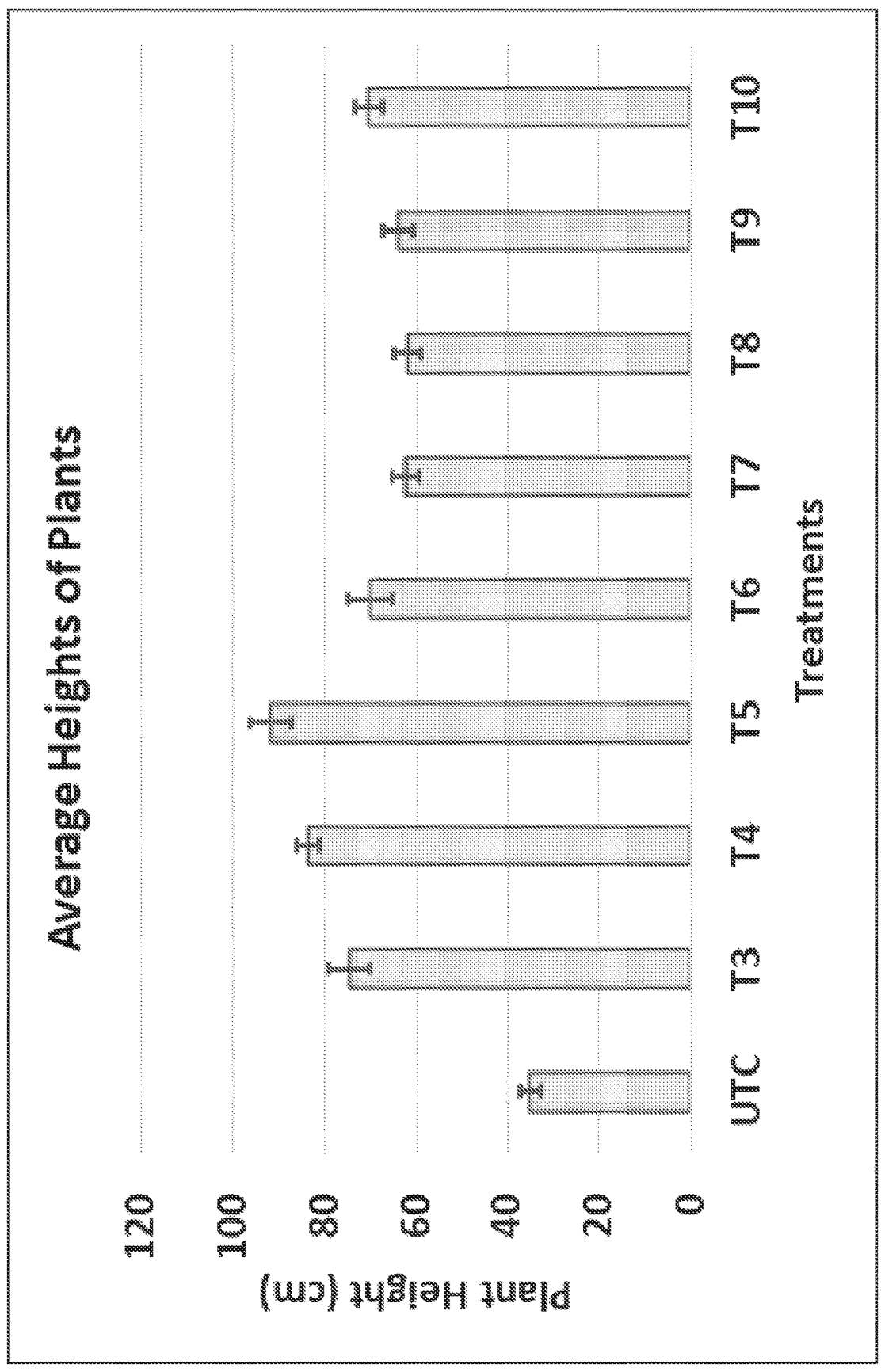
FIG. 3 depicts average heights of UTC and treated soy plants inoculated with different concentrations of fungal cultures. Error bars indicate SE.

Plant health was recorded based on the visual observations where control plants were yellowish and growth retarded. However, treatments with *Leptodontidium orchidicola* DMTR-CTR-4873 (3 concentrations), *Thozetella nivea* DMTR-CTR-2359 (3 concentration) and *Trichoderma longipile* DMTR-CTR-1291 (2 treatments) were fully healthy (FIG. 1). Plant heights were also increased in soybeans inoculated with the fungi (FIG. 3).

Leaf and Pod Observations

Figure 4:
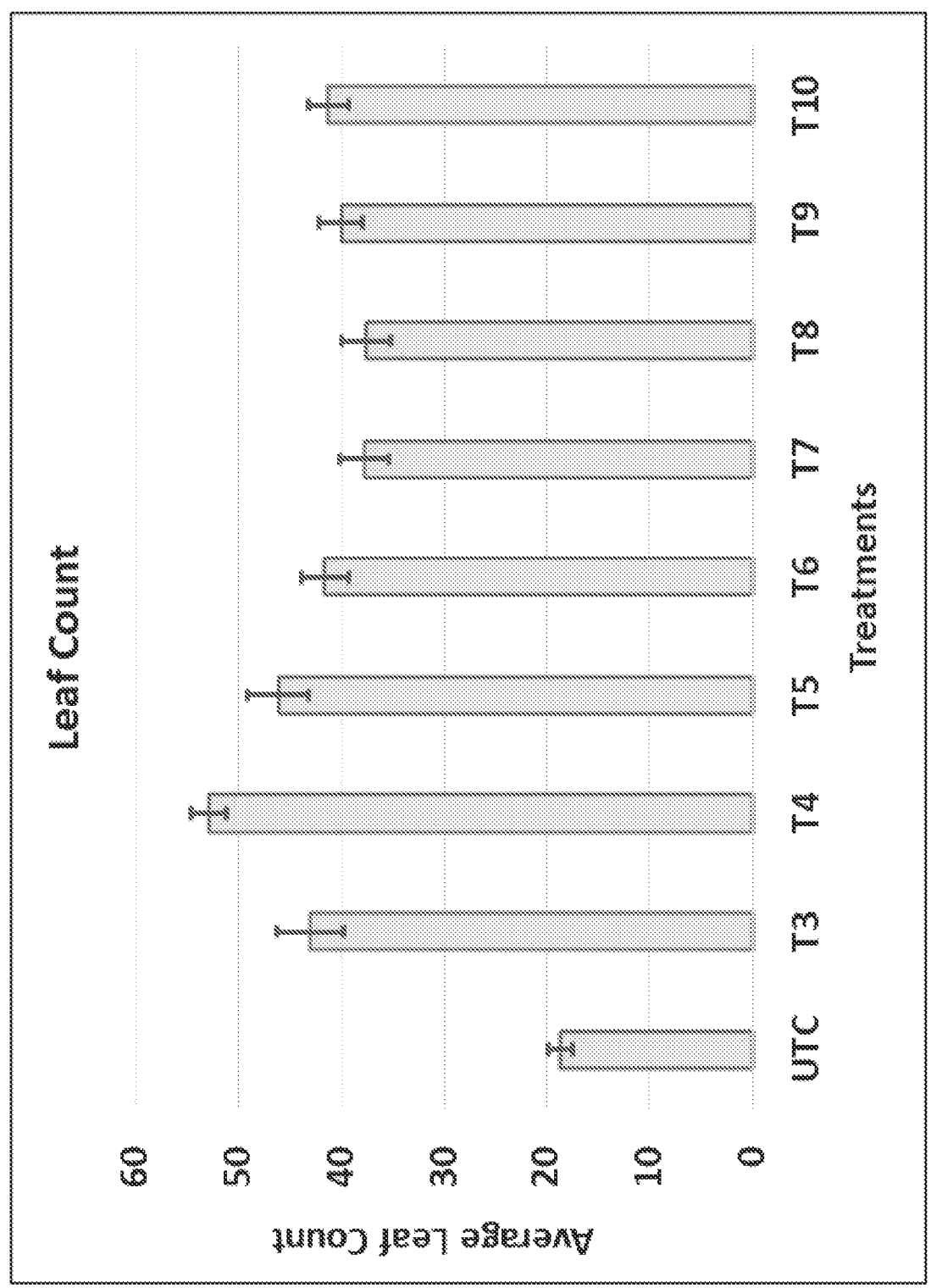
FIG. 4 depicts average leaf counts of UTC and treated soy plants inoculated with different concentrations of fungal cultures. Error bars indicate SE.
Figure 5:
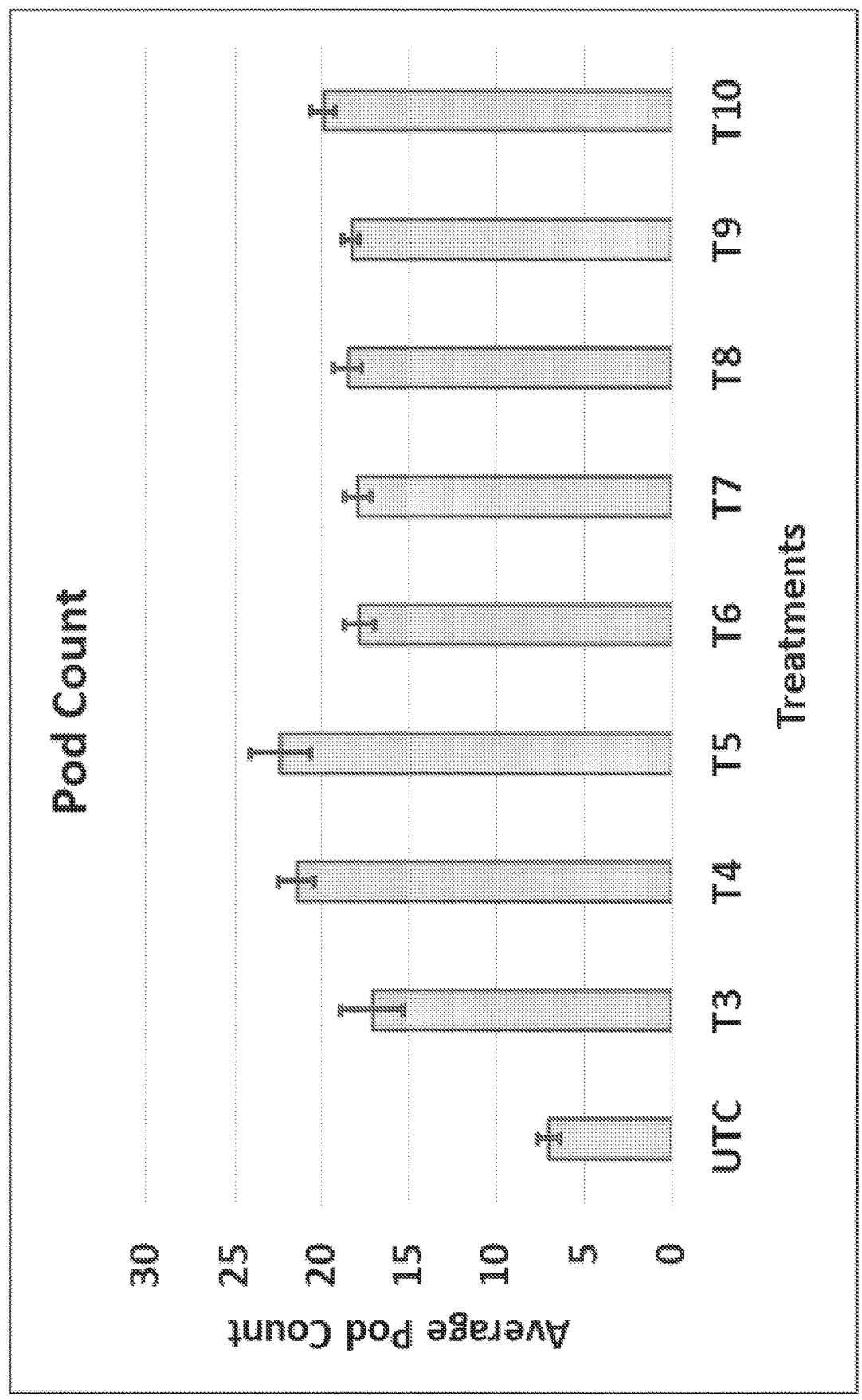
FIG. 5 depicts average pod counts of UTC and treated soy plants inoculated with different concentrations of fungal cultures. Error bars indicate SE.

Throughout the experiment a total number of leaves and pods were recorded. FIG. 4 shows the average number of leaves, and FIG. 5 shows the average number of pods from untreated control and treated plants. The number of leaves and pods were significantly greater in treated plants compared to the untreated control plants.

Soil, Root, Nodules, and Leaf Harvesting

Interim soil and tissue harvesting: A small soil corer was used to harvest the soil from the rhizospheric regions. Harvested soil was mixed properly and divided into aliquots. This harvested soil also contains root particles and nodules. One aliquot was processed for drying at 42° C. and will be analysed for total organic carbon (TOC).

Figure 6:
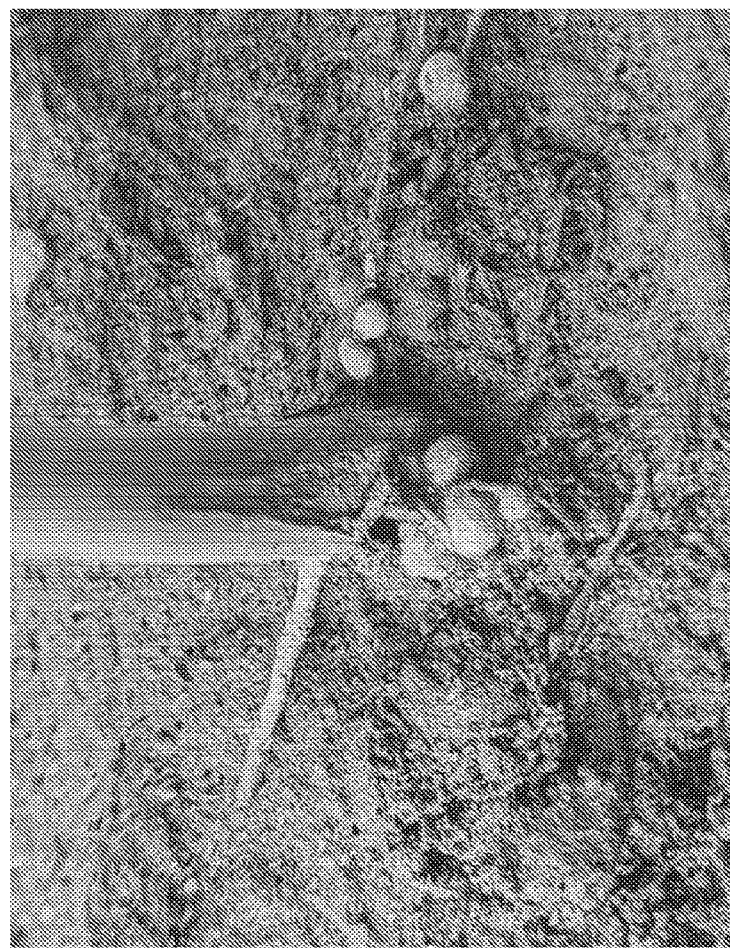
FIG. 6 depicts representative photographs of the nodulation frequency and appearance of nodules in untreated control and treated soy plants inoculated with fungal cultures.
Figure 6:

Apart from the soil, nodule appearance was also observed. FIG. 6 shows the general pattern and occurrence of nodules in untreated control and treatment pots. As per the observations made at the time of interim soil harvesting and data collection, untreated control plants showed much fewer nodules and smaller nodules compared to the treated plants.

Additional measurements of the size and number of nodules will be noted at the time of trial termination.

A portion of roots and nodules along with the rhizospheric soil was harvested, frozen in liquid nitrogen and stored at −80° C. for molecular analyses. These analyses will include observations related to confirmation of colonisation by the fungal strains.

GENERAL DISCUSSION

A soil type very close to the soil profile of soybean growing regions of Australia, (River Loam, sourced from a soil supplier in New South Wales) was used in this study. Untreated control plants were inoculated only with *rhizobium*. However, treated plants were inoculated with both *rhizobium* and fungal isolates. Growth retardation and yellowing was observed in the untreated control plants while plants from all three treatments were healthy, green and produced more biomass. The heights of treated plants were greater compared to the untreated control plants. In addition, total chlorophyll content, number of leaves, and number of pods were higher in the treated plants.

The severe yellowing observed in untreated control plants could be due to the inability of these plants to fix nitrogen due to decreased nodule formation. In contrast, in the treated plants the *rhizobium* and fungal combinations enabled the *rhizobium* to become established, and this enabled plant roots to form more nodules. The results suggest that more nodules in treated plants helped these plants in nitrogen fixation and healthy growth. Importantly, the success of the fungal-bacterial-root interactions provides healthy conditions for plants to grow and produce more exudates and the fungal isolates to sequester more carbon in the soil.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of increasing organic carbon in a soil, comprising:
inoculating the soil and/or a plant growing in the soil with a fungal strain from a species of *Clonostachys rosea*, wherein the fungal strain is in an effective amount to increase organic carbon in the soil compared to a non-inoculated control soil, and wherein the fungal strain is *Clonostachys rosea* DMTR-CTR-US-173 (ATCC Accession No. PTA-127299) or *Clonostachys rosea* DMTR-CTR-1081 (NMI Accession No. V22/003495).

2. The method of claim 1, further comprising an initial step of identifying the soil as having a soil organic carbon (SOC) level below a threshold.

3. The method of claim 2, wherein the threshold is a SOC level below 5%, 4%, 3%, 2%, 1%, 0.9%, 0.8%, 0.7%, 0.6%, 0.5%, 0.4%, 0.3%, 0.2%, or 0.1%.

4. The method of claim 1, wherein the soil and/or plant are non-native to the fungal strain.

5. The method of claim 4, wherein the non-native plant is selected from the group consisting of wheat, rice, corn (maize), rye, oats, barley, sorghum, millet, flax, hemp, jute, cotton, soybeans, alfalfa, clover, peanuts, lentils, lupins, peas, canola, and chickpea.

6. The method of claim 1, further comprising inoculating the soil and/or plant growing in the soil with one or more fungal strains from at least one genus selected from the group consisting of *Acrocalymma, Leptodontidium, Periconia, Phaeosphaeria, Thozetella, Trichoderma*, and a combination thereof.

7. The method of claim 6, wherein the one or more fungal strains are from a species selected from the group consisting of *Acrocalymma vagum, Leptodontidium orchidicola, Periconia* sp., *Periconia macrospinosa, Phaeosphaeria luctuosa, Phaeosphaeria vagans, Thozetella nivea, Trichoderma hamatum, Trichoderma longipile, Trichoderma spirale*, and a combination thereof.

8. The method of claim 7, wherein the one or more fungal strains are selected from the group consisting of *Acrocalymma vagum* DMTR-CTR-11556 (NMI Accession No. V22/006357), *Leptodontidium orchidicola* DMTR-CTR-4873 (NMI Accession No. V22/003497), *Periconia* sp. DMTR-CTR-6649 (NMI Accession No. V22/006356), *Periconia macrospinosa* DMTR-CTR-US-125 (ATCC Accession No. PTA-127300), *Periconia macrospinosa* DMTR-CTR-1852 (NMI Accession No. V22/006358), *Phaeosphaeria luctuosa/vagans* DMTR-CTR-3044 (NMI Accession No. V22/006355), *Thozetella nivea* DMTR-CTR-2359 (NMI Accession No. V22/003496), *Trichoderma hamatum* DMTR-CTR-US-73 (ATCC Accession No. PTA-127301), *Trichoderma longipile /spirale* DMTR-CTR-1291 (NMI Accession No. V22/006354), and a combination thereof.

9. The method of claim 1, wherein the fungal strain is formulated as (a) a solid, liquid or gel; (b) a powder, pellet or granules; or (c) an emulsion, colloid, suspension or solution.

10. The method of claim 1, wherein the fungal strain is formulated at a concentration of at least $10^3$ colony forming units (CFU) per millilitre or gram.

11. The method of claim 1, wherein the fungal strain is applied or coated on at least a portion of an outer surface of a plant, plant part or plant seed.

12. The method of claim 1, wherein inoculation with the fungal strain increases recalcitrant aggregate carbon or mineral associated organic matter carbon in the soil.

13. A method for sequestering atmospheric carbon for storage as organic carbon in a soil, comprising:
inoculating the soil and/or a plant growing in the soil with a fungal strain from a species of *Clonostachys rosea*, wherein the fungal strain is in an effective amount to increase sequestered atmospheric carbon in the soil compared to a non-inoculated control soil.

14. The method of claim 13, wherein the plant is a non-native plant selected from the group consisting of wheat, rice, corn (maize), rye, oats, barley, sorghum, millet, flax, hemp, jute, cotton, soybeans, alfalfa, clover, peanuts, lentils, lupins, peas, canola and chickpea.

15. The method of claim 13, further comprising inoculating the soil and/or plant growing in the soil with one or more fungal strains from at least one genus selected from the group consisting of *Acrocalymma, Leptodontidium, Periconia, Phaeosphaeria, Thozetella, Trichoderma*, and a combination thereof.

16. The method of claim 15, wherein the one or more fungal strains are from a species selected from the group consisting of *Acrocalymma vagum, Leptodontidium orchidicola, Periconia* sp., *Periconia macrospinosa, Phaeosphaeria luctuosa, Phaeosphaeria vagans, Thozetella nivea, Trichoderma hamatum, Trichoderma longipile, Trichoderma spirale*, and a combination thereof.

17. The method of claim 16, wherein the one or more fungal strains are selected from the group consisting of *Acrocalymma vagum* DMTR-CTR-11556 (NMI Accession No. V22/006357), *Leptodontidium orchidicola* DMTR-CTR-4873 (NMI Accession No. V22/003497), *Periconia* sp. DMTR-CTR-6649 (NMI Accession No. V22/006356), *Periconia macrospinosa* DMTR-CTR-US-125 (ATCC Accession No. PTA-127300), *Periconia macrospinosa* DMTR-CTR-1852 (NMI Accession No. V22/006358), *Phaeosphaeria luctuosa/vagans* DMTR-CTR-3044 (NMI Accession No. V22/006355), *Thozetella nivea* DMTR-CTR-2359 (NMI Accession No. V22/003496), *Trichoderma hamatum* DMTR-CTR-US-73 (ATCC Accession No. PTA-127301), *Trichoderma longipile /spirale* DMTR-CTR-1291 (NMI Accession No. V22/006354), and a combination thereof.

18. The method of claim 13, wherein the fungal strain is formulated as (a) a solid, liquid or gel; (b) a powder, pellet or granules; or (c) an emulsion, colloid, suspension or solution.

19. The method of claim 13, wherein the fungal strain is formulated at a concentration of at least $10^3$ colony forming units (CFU) per millilitre or gram.

20. The method of claim 13, wherein the fungal strain is applied or coated on at least a portion of an outer surface of a plant, plant part or plant seed.

21. The method of claim 13, wherein inoculation with the fungal strain increases recalcitrant aggregate carbon or mineral associated organic matter carbon in the soil.

22. A method for sequestering atmospheric carbon for storage as organic carbon in a recalcitrant form in a soil, comprising:
inoculating the soil and/or a plant growing in the soil with a fungal strain from a species of *Clonostachys rosea*, wherein the fungal strain is in an effective amount to increase sequestered atmospheric carbon in the soil compared to a non-inoculated control soil , and wherein the fungal strain is *Clonostachys rosea* DMTR-CTR-US-173 (ATCC Accession No. PTA-127299) or *Clonostachys rosea* DMTR- CTR-1081 (NMI Accession No. V22/003495).

23. The method of claim 22, wherein the plant is a non-native plant selected from the group consisting of wheat, rice, corn (maize), rye, oats, barley, sorghum, millet, flax, hemp, jute, cotton, soybeans, alfalfa, clover, peanuts, lentils, lupins, peas, canola and chickpea.

24. The method of claim 22, wherein the recalcitrant form is aggregate carbon (AggC) and/or mineral associated organic matter carbon (MAOM).

25. The method of claim 22, further comprising inoculating the soil and/or plant growing in the soil with one or more fungal strains selected from the group consisting of *Acrocalymma vagum* DMTR-CTR-11556 (NMI Accession No. V22/006357), *Leptodontidium orchidicola* DMTR-CTR-4873 (NMI Accession No. V22/003497), *Periconia* sp. DMTR-CTR-6649 (NMI Accession No. V22/006356), *Periconia macrospinosa* DMTR-CTR-US-125 (ATCC Accession No. PTA-127300), *Periconia macrospinosa* DMTR-CTR-1852 (NMI Accession No. V22/006358), *Phaeosphaeria luctuosa/vagans* DMTR-CTR-3044 (NMI Accession No. V22/006355), *Thozetella nivea* DMTR-CTR-2359 (NMI Accession No. V22/003496), *Trichoderma hamatum* DMTR-CTR-US-73 (ATCC Accession No. PTA-127301), *Trichoderma longipile/spirale* DMTR-CTR-1291 (NMI Accession No. V22/006354), and a combination thereof.

26. The method of claim 22, wherein the fungal strain is formulated as (a) a solid, liquid or gel; (b) a powder, pellet or granules; or (c) an emulsion, colloid, suspension or solution.

27. The method of claim 22, wherein the fungal strain is formulated at a concentration of at least $10^3$ colony forming units (CFU) per millilitre or gram.

* * * * *

UNITED STATES PATENT AND TRADEMARK OFFICE
CERTIFICATE OF CORRECTION

| | |
|---|---|
| PATENT NO. | : 12,017,967 B2 |
| APPLICATION NO. | : 18/406089 |
| DATED | : June 25, 2024 |
| INVENTOR(S) | : Ray Riley et al. |

It is certified that error appears in the above-identified patent and that said Letters Patent is hereby corrected as shown below:

In the Claims

At Column 53, Line 13, before the "." in Claim 13 please insert: -- , and wherein the fungal strain is Clonostachys rosea DMTR-CTR-US-173 (ATCC Accession No. PTA-127299) or Clonostachys rosea DMTR-CTR-1081 (NMI Accession No. V22/003495) --.

Signed and Sealed this
Sixth Day of August, 2024

Katherine Kelly Vidal
*Director of the United States Patent and Trademark Office*

SEQUENCE LISTING

```
Sequence total quantity: 19
SEQ ID NO: 1             moltype = DNA  length = 341
FEATURE                  Location/Qualifiers
source                   1..341
                         mol_type = other DNA
                         organism = synthetic construct
SEQUENCE: 1
gcatcgatga agaacgcagc gaaatgcgat aagtagtgtg aattgcagaa ttcagtgaat    60
catcgaatct ttgaacgcac attgcgcccc ttggtattcc atggggcatg cctgttcgag   120
cgtcatttga accctcaagc tctgcttggt gttgggtgtt tgtcccgcca ttgcgcgtgg   180
actcgcctta aagcaattgg cagccatgta atccggcttt gagcgcagca cattgcgtac   240
tctctactgg gacatgggca tccagaagcc ttatttttta ctcttgacct cggatcaggt   300
agggataccc gctgaactta agcatatcaa taagcggagg a                       341

SEQ ID NO: 2             moltype = DNA  length = 341
FEATURE                  Location/Qualifiers
source                   1..341
                         mol_type = other DNA
                         organism = synthetic construct
SEQUENCE: 2
gcatcgatga agaacgcagc gaaatgcgat aagtagtgtg aattgcagaa ttcagtgaat    60
catcgaatct ttgaacgcac attgcgcccc ttggtattcc atggggcatg cctgttcgag   120
cgtcatttga accctcaagc tctgcttggt gttgggtgtt tgtcccgcca ttgcgcgtgg   180
actcgcctta aagcaattgg cagccatgta atccggcttt gagcgcagca cattgcgtac   240
tctctactgg gacatgggca tccagaagcc ttatttttta ctcttgacct cggatcaggt   300
agggataccc gctgaactta agcatatcaa taagcggagg a                       341

SEQ ID NO: 3             moltype = DNA  length = 353
FEATURE                  Location/Qualifiers
source                   1..353
                         mol_type = other DNA
                         organism = synthetic construct
SEQUENCE: 3
gcatcgatga agaacgcagc gaaatgcgat aagtaatgtg aattgcagaa ttcagtgaat    60
catcgaatct ttgaacgcac attgcgcccg ccagtattct ggcgggcatg cctgtctgag   120
cgtcatttca accctcatgc ccctagggcg tggtgttggg gatcggccaa agcccgcgag   180
ggacggccgg cccctaaatc tagtggcgga cccgtcgtgg cctcctctgc gaagtagtga   240
tattccgcat cggagagcga cgagccctg ccgttaaacc cccaactttc caaggttgac   300
ctcagatcag gtaggaatac ccgctgaact taagcatatc aataagcgga gga          353

SEQ ID NO: 4             moltype = DNA  length = 353
FEATURE                  Location/Qualifiers
source                   1..353
                         mol_type = other DNA
                         organism = synthetic construct
SEQUENCE: 4
gcatcgatga agaacgcagc gaaatgcgat aagtaatgtg aattgcagaa ttcagtgaat    60
catcgaatct ttgaacgcac attgcgcccg ccagtattct ggcgggcatg cctgtctgag   120
cgtcatttca accctcatgc ccctagggcg tggtgttggg gatcggccaa agcccgcgag   180
ggacggccgg cccctaaatc tagtggcgga cccgtcgtgg cctcctctgc gaagtagtga   240
tattccgcat cggagagcga cgagccctg ccgttaaacc cccaactttc caaggttgac   300
```

```
ctcagatcag gtaggaatac ccgctgaact taagcatatc aataagcgga gga            353

SEQ ID NO: 5            moltype = DNA   length = 335
FEATURE                 Location/Qualifiers
source                  1..335
                        mol_type = other DNA
                        organism = synthetic construct
SEQUENCE: 5
gcatcgatga agaacgcagc gaaatgcgat aagtaatgtg aattgcagaa ttcagtgaat     60
catcgaatct ttgaacgcac attgcgccct ctggtattcc gggggggcatg cctgttcgag   120
cgtcattata accactcaag ctctcgcttg gtattggggt tcgcggtttc gcggccccta   180
aaatcagtgg cggtgcctgt cggctctacg cgtagtaata ctcctcgcga ttgagtccgg   240
taggtctact tgccagcaac ccctaatttt tttaaggttg acctcggatc aggtagggat   300
acccgctgaa cttaagcata tcaataagcg gagga                              335

SEQ ID NO: 6            moltype = DNA   length = 335
FEATURE                 Location/Qualifiers
source                  1..335
                        mol_type = other DNA
                        organism = synthetic construct
SEQUENCE: 6
gcatcgatga agaacgcagc gaaatgcgat aagtaatgtg aattgcagaa ttcagtgaat     60
catcgaatct ttgaacgcac attgcgccct ctggtattcc gggggggcatg cctgttcgag   120
cgtcattata accactcaag ctctcgcttg gtattggggt tcgcggtttc gcgacccccta   180
aaatcagtgg cggtgcctgt cggctctacg cgtagtaata ctcctcgcga ttgagtccgg   240
taggtctact tgccagcaac ccctaatttt tttaaggttg acctcggatc aggtagggat   300
acccgctgaa cttaagcata tcaataagcg gagga                              335

SEQ ID NO: 7            moltype = DNA   length = 347
FEATURE                 Location/Qualifiers
source                  1..347
                        mol_type = other DNA
                        organism = synthetic construct
SEQUENCE: 7
gcatcgatga agaacgcagc gaaatgcgat aagtagtgtg aattgcagaa ttcagtgaat     60
catcgaatct ttgaacgcac attgcggcca taggtattcc tttggccatg cctgttcgag   120
cgtcatttac accctcaagc ctagcttggt gttgggcgtc tgtcccgccg ttttcgcgcg   180
cggactcgcc tcaaagtcat tggcggcggt cgtgccggcc cctcgcgca gcacatttgc    240
gcttctcgga ggcccggcgg atccgcgctc agcaagacc tttcacgact tgacctcgga    300
tcaggtaggg atacccgctg aacttaagca tatcaataag cggagga                 347

SEQ ID NO: 8            moltype = DNA   length = 347
FEATURE                 Location/Qualifiers
source                  1..347
                        mol_type = other DNA
                        organism = synthetic construct
SEQUENCE: 8
gcatcgatga agaacgcagc gaaatgcgat aagtagtgtg aattgcagaa ttcagtgaat     60
catcgaatct ttgaacgcac attgcggcca taggtattcc tttggccatg cctgttcgag   120
cgtcatttac accctcaagc ctagcttggt gttgggcgtc tgtcccgccg ttctcgcgcg   180
cggactcgcc tcaaagtcat tggcggcggt cgtgccggcc cctcgcgca gcacatttgc    240
gcttctcgga ggcccggcgg atccgcgctc agcaagacc tttcacgact tgacctcgga    300
tcaggtaggg atacccgctg aacttaagca tatcaataag cggagga                 347

SEQ ID NO: 9            moltype = DNA   length = 345
FEATURE                 Location/Qualifiers
source                  1..345
                        mol_type = other DNA
                        organism = synthetic construct
SEQUENCE: 9
gcatcgatga agaacgcagc gaaatgcgat aagtagtgtg aattgcagaa ttcagtgaat     60
catcgaatct ttgaacgcac attgcggcca tagggtattc ctttggccat gcctgttcga   120
gcgtcattta caccctcaag cctagcttgg tgttgggcgt ctgtcccgct tcgcgcgcgg   180
actcgcctca aagtcattgg cggcgtcgt gccggcccga gcgcagca catttgcgct     240
tctcggaggc ccggcggacc cgcgctccag caagaccttt ctacgacttg acctcggatc  300
aggtagggat acccgctgaa cttaagcata tcaataagcg gagga                  345

SEQ ID NO: 10           moltype = DNA   length = 303
FEATURE                 Location/Qualifiers
source                  1..303
                        mol_type = other DNA
                        organism = synthetic construct
SEQUENCE: 10
gcatcgatga agaacgcagc gaaatgcgat aagtagtgtg aattgcagaa ttcagtgaat     60
catcgaatct ttgaacgcac attgcggcca taggtattcc tttggccatg cctgttcgag   120
cgtcatttac accctcaagc ctagcttggt gttgggcgtc tgtcccgccg ttctcgcgcg   180
cggactcgcc tcaaagtcat tggcggcggt cgtgccggcc cctcgcgca gcacatttgc    240
gcttctcgga ggcccggcgg atccgcgctc agcaagacc tttcacgact tgacctcgga    300
tca                                                                 303
```

```
SEQ ID NO: 11              moltype = DNA   length = 347
FEATURE                    Location/Qualifiers
source                     1..347
                           mol_type = other DNA
                           organism = synthetic construct
SEQUENCE: 11
gcatcgatga agaacgcagc gaaatgcgat aagtagtgtg aattgcagaa ttcagtgaat    60
catcgaatct ttgaacgcac attgcggcca taggtattcc tttggccatg cctgttcgag   120
cgtcatttac accctcaagc ctagcttggt gttgggcgtc tgtcccgccg ttctcgcgcg   180
cggactcgcc tcaaagtcat tggcggcggt cgtgccggcc ccctcgcgca gcacatttgc   240
gcttctcgga ggcccggcgg atccgcgctc agcaagacc tttcacgact tgacctcgga   300
tcaggtaggg atacccgctg aacttaagca tatcaataag cggagga               347

SEQ ID NO: 12              moltype = DNA   length = 345
FEATURE                    Location/Qualifiers
source                     1..345
                           mol_type = other DNA
                           organism = synthetic construct
SEQUENCE: 12
gcatcgatga agaacgcagc gaaatgcgat aagtagtgtg aattgcagaa ttcagtgaat    60
catcgaatct ttgaacgcac attgcggcca tagggtattc ctttggccat gcctgttcga   120
gcgtcattta cacccctcaag cctagcttgg tgttgggcgt ctgtcccgct tcgcgcgcg   180
actcgcctca aagtcattgg cggcggtcgt gccggcccct gagcgcagca catttgcgct   240
tctcggaggc ccggcggacc cgcgctccag caagaccttt ctacgacttg acctcggatc   300
aggtagggat acccgctgaa cttaagcata tcaataagcg gagga                 345

SEQ ID NO: 13              moltype = DNA   length = 341
FEATURE                    Location/Qualifiers
source                     1..341
                           mol_type = other DNA
                           organism = synthetic construct
SEQUENCE: 13
gcatcgatga agaacgcagc gaaatgcgat aagtagtgtg aattgcagaa ttcagtgaat    60
catcgaatct ttgaacgcac attgcgcccc ttggtattcc atggggcatg cctgttcgag   120
cgtcatttgt accctcaagc tctgcttggt gttgggtgtt tgtcctctcc tttgcgtttg   180
gactcgcctt aaagcaattg gcagccagtg ttttggtatt gaagcgcagc acattttgcg   240
attctagccg ataatacttg cgtccataag ccttttttca cttttgacct cggatcaggt   300
agggataccc gctgaactta agcatatcaa taagcggagg a                     341

SEQ ID NO: 14              moltype = DNA   length = 339
FEATURE                    Location/Qualifiers
source                     1..339
                           mol_type = other DNA
                           organism = synthetic construct
SEQUENCE: 14
gcatcgatga agaacgcagc gaaatgcgat aagtaatgtg aattgcagaa ttcagtgaat    60
catcgaatct ttgaacgcac attgcgcccc ccggtattcc ggcgggcatg cctgttcgag   120
cgtcatttca accctcaggc ctcgcctggt gttggggctc ctgcgcactg caggccctca   180
aaggcagcgc gggtgcgcc tacgaaccga acgcagtagt tttctctcgt tctggtctcg    240
cgggcgtgct ccggccgtta aaccccctt atatccaatg gttgacctcg gatcaggtag    300
gaatacccgc tgaacttaag catatcaata agcggagga                        339

SEQ ID NO: 15              moltype = DNA   length = 358
FEATURE                    Location/Qualifiers
source                     1..358
                           mol_type = other DNA
                           organism = synthetic construct
SEQUENCE: 15
gcatcgatga agaacgcagc gaaatgcgat aagtaatgtg aattgcagaa ttcagtgaat    60
catcgaatct ttgaacgcac attgcgcccg ccagtattct ggcgggcatg cctgtccgag   120
cgtcatttca accctcgaac ccctcggggg atcggcgtt ggggatcggg acccctcacc   180
gggtgccggc cctgaaatac agtggcggtc tcgccgcagc ctctcctgcg cagtagtttg   240
cacaactcgc accgggagcg cggcgcgtcc acgtccgtaa acacccaac ttctgaaatg    300
ttgacctcgg atcaggtagg aatacccgct gaacttaagc atatcaataa gcggagga    358

SEQ ID NO: 16              moltype = DNA   length = 361
FEATURE                    Location/Qualifiers
source                     1..361
                           mol_type = other DNA
                           organism = synthetic construct
SEQUENCE: 16
gcatcgatga agaacgcagc gaaatgcgat aagtaatgtg aattgcagaa ttcagtgaat    60
catcgaatct ttgaacgcac attgcgcccg ccagtattct ggcgggcatg cctgtccgag   120
cgtcatttca accctcgaac ccctcggggg gtcggcgtt ggggatcggg aacccctaag    180
acgggatccc ggccccgaaa tacagtggcg gtctcgccgc agcctctcct gcgcagtagt   240
ttgcacaact cgcaccggga gcgcggcgcg tccacgtccg taaaacaccc aacttctgaa   300
atgttgacct cggatcaggt aggaatacc gctgaactta agcatatcaa taagcggagg   360
a                                                                 361
```

-continued

```
SEQ ID NO: 17          moltype = DNA  length = 354
FEATURE                Location/Qualifiers
source                 1..354
                       mol_type = other DNA
                       organism = synthetic construct
SEQUENCE: 17
gcatcgatga agaacgcagc gaaatgcgat aagtaatgtg aattgcagaa ttcagtgaat    60
catcgaatct ttgaacgcac attgcgcccg ccagtattct ggcgggcatg cctgtccgag   120
cgtcatttca accctcgaac ccctccgggg ggtcggcgtt ggggatcggc ccttcacggg   180
gccggccccg aaatacagtg gcggtctcgc cgcagcctct cctgcgcagt agtttgcaca   240
ctcgcatcgg gagcgcggcg cgtccattgc cgtaaaacac ccaactttct gaaatgttga   300
cctcggatca ggtaggaata cccgctgaac ttaagcatat caataagcgg agga         354

SEQ ID NO: 18          moltype = DNA  length = 355
FEATURE                Location/Qualifiers
source                 1..355
                       mol_type = other DNA
                       organism = synthetic construct
SEQUENCE: 18
gcatcgatga agaacgcagc gaaatgcgat aagtaatgtg aattgcagaa ttcagtgaat    60
catcgaatct ttgaacgcac attgcgcccg ccagtattct ggcgggcatg cctgtccgag   120
cgtcatttca accctcgaac ccctccgggg ggtcggcgtt ggggatcggc cctttacggg   180
gccggccccg aaatacagtg gcggtctcgc cgcagcctct cctgcgcagt agtttgcaca   240
ctcgcatcgg gagcgcggcg cgtccacagc cgttaaacac cccaaacttc tgaaatgttg   300
acctcggatc aggtaggaat acccgctgaa cttaagcata tcaataagcg gagga        355

SEQ ID NO: 19          moltype = DNA  length = 361
FEATURE                Location/Qualifiers
source                 1..361
                       mol_type = other DNA
                       organism = synthetic construct
SEQUENCE: 19
gcatcgatga agaacgcagc gaaatgcgat aagtaatgtg aattgcagaa ttcagtgaat    60
catcgaatct ttgaacgcac attgcgcccg ccagtattct ggcgggcatg cctgtccgag   120
cgtcatttca accctcgaac ccctccgggg gtccggcgtt ggggatcggg aacccctaag   180
acgggatccc ggcccgaaa tacagtggcg gtctcgccgc agcctctcct gcgcagtagt   240
ttgcacaact cgcaccggga gcgcggcgcg tccacgtccg taaaacaccc aacttctgaa   300
atgttgacct cggatcaggt aggaatacccc gctgaactta agcatatcaa taagcggagg   360
a                                                                   361
```